US008501890B2

(12) United States Patent
Pearson et al.

(10) Patent No.: US 8,501,890 B2
(45) Date of Patent: Aug. 6, 2013

(54) COPOLYMERIZABLE METHINE AND ANTHRAQUINONE COMPOUNDS AND ARTICLES CONTAINING THEM

(71) Applicant: Abbott Medical Optics Inc., Santa Ana, CA (US)

(72) Inventors: Jason Clay Pearson, Kingsport, TN (US); Max Allen Weaver, Kingsport, TN (US); Jean Carroll Fleischer, Kingsport, TN (US); Gregory Allan King, Mount Carmel, TN (US)

(73) Assignee: Abbott Medical Optics Inc., Santa Ana, CA (US)

( * ) Notice: Subject to any disclaimer, the term of this patent is extended or adjusted under 35 U.S.C. 154(b) by 0 days.

(21) Appl. No.: 13/622,160

(22) Filed: Sep. 18, 2012

(65) Prior Publication Data
US 2013/0018159 A1 Jan. 17, 2013

Related U.S. Application Data

(60) Division of application No. 12/257,277, filed on Oct. 23, 2008, now Pat. No. 8,360,576, which is a continuation of application No. 11/271,382, filed on Nov. 10, 2005, now abandoned.

(60) Provisional application No. 60/629,556, filed on Nov. 22, 2004.

(51) Int. Cl.
C08F 12/26 (2006.01)
C08F 12/30 (2006.01)

(52) U.S. Cl.
USPC ........... 526/299; 526/258; 526/286; 526/288; 526/298; 526/303.1; 526/304; 526/305; 526/310

(58) Field of Classification Search
USPC .............. 526/258, 286, 288, 298, 299, 303.1, 526/304, 305, 310
See application file for complete search history.

(56) References Cited

U.S. PATENT DOCUMENTS

| 3,841,878 | A | 10/1974 | Pollet et al. |
|---|---|---|---|
| 4,304,895 | A | 12/1981 | Loshaek |
| 4,390,676 | A | 6/1983 | Loshaek |
| 4,528,311 | A | 7/1985 | Beard et al. |
| 4,617,374 | A | 10/1986 | Pruett et al. |
| 4,636,212 | A | 1/1987 | Posin et al. |
| 4,681,412 | A | 7/1987 | Lemelson |
| 4,716,234 | A | 12/1987 | Dunks et al. |
| 4,737,322 | A | 4/1988 | Bruns et al. |
| 4,753,654 | A | 6/1988 | Posin et al. |
| 4,863,466 | A | 9/1989 | Schlegel |
| 4,929,250 | A | 5/1990 | Hung et al. |
| 4,955,904 | A | 9/1990 | Atebara et al. |
| 4,963,160 | A | 10/1990 | Hung et al. |
| 4,998,817 | A | 3/1991 | Zeltzer |
| 5,008,102 | A | 4/1991 | York |
| 5,047,447 | A | 9/1991 | Gallas |
| 5,098,445 | A | 3/1992 | Hung et al. |
| 5,120,120 | A | 6/1992 | Cohen |
| 5,172,256 | A | 12/1992 | Sethofer et al. |
| 5,235,358 | A | 8/1993 | Mutzhas et al. |
| 5,269,813 | A | 12/1993 | Yoshida et al. |
| 5,272,151 | A | 12/1993 | Marzi et al. |
| 5,298,033 | A | 3/1994 | Hung et al. |
| 5,374,663 | A | 12/1994 | Daicho et al. |
| 5,376,650 | A | 12/1994 | Weaver et al. |
| 5,399,692 | A | 3/1995 | Hung et al. |
| 5,470,932 | A | 11/1995 | Jinkerson |
| 5,500,024 | A | 3/1996 | Hung et al. |
| 5,528,322 | A | 6/1996 | Jinkerson |
| 5,534,041 | A | 7/1996 | Havens et al. |
| 5,543,504 | A | 8/1996 | Jinkerson |
| 5,657,726 | A | 8/1997 | Diggs |
| 5,662,707 | A | 9/1997 | Jinkerson |
| 5,846,457 | A | 12/1998 | Hoffman |
| 5,866,635 | A | 2/1999 | Collins et al. |
| 5,922,246 | A | 7/1999 | Matsushita et al. |
| 6,143,028 | A | 11/2000 | Galin et al. |
| 6,158,862 | A | 12/2000 | Patel et al. |
| 6,187,042 | B1 | 2/2001 | Sheets, Jr. et al. |
| 6,224,210 | B1 | 5/2001 | Chateau et al. |
| 6,242,551 | B1 | 6/2001 | Tsuzuki et al. |
| 6,244,707 | B1 | 6/2001 | Faubl |
| 6,277,940 | B1 | 8/2001 | Niwa et al. |
| 6,280,471 | B1 | 8/2001 | Peyman et al. |
| 6,305,801 | B1 | 10/2001 | Kerns, Jr. et al. |
| 6,310,215 | B1 | 10/2001 | Iwamoto |
| 6,326,448 | B1 | 12/2001 | Ojio et al. |
| 6,387,127 | B1 | 5/2002 | Muller-Lierheim |
| 6,399,805 | B2 | 6/2002 | Wolf et al. |
| 6,432,137 | B1 | 8/2002 | Nanushyan et al. |
| 6,604,824 | B2 | 8/2003 | Larson |
| 7,098,283 | B2 | 8/2006 | Lai |
| 7,232,896 | B2 | 6/2007 | Miki et al. |
| 7,241,312 | B2 | 7/2007 | Lai et al. |
| 7,278,737 | B2 | 10/2007 | Mainster et al. |

(Continued)

FOREIGN PATENT DOCUMENTS

| AU | 2004312897 | 7/2005 |
|---|---|---|
| DE | 3428895 A1 | 2/1986 |

(Continued)

OTHER PUBLICATIONS

Cho H., et al., "Novel Caffeic Acid Derivatives: Extremely Potent Inhibitors of 12-Lipoxygenase," Journal of Medicinal Chemistry, 1991, vol. 34 (4), pp. 1503-1505.

(Continued)

Primary Examiner — Vu A Nguyen
(74) Attorney, Agent, or Firm — Abbott Medical Optics Inc.

(57) ABSTRACT

This invention relates to polymerizable ultraviolet light absorbers and yellow colorants and their use in ophthalmic lenses. In particular, this invention relates to polymerizable ultraviolet light absorbing methane compounds and yellow compounds of the methine and anthraquinone classes that block ultraviolet light and/or violet-blue light transmission through ophthalmic lenses.

11 Claims, No Drawings

U.S. PATENT DOCUMENTS

| | | | |
|---|---|---|---|
| 7,677,725 | B2 | 3/2010 | Piers et al. |
| 2002/0042653 | A1 | 4/2002 | Copeland et al. |
| 2002/0082312 | A1 | 6/2002 | Lai |
| 2003/0078359 | A1 | 4/2003 | Ichinohe |
| 2003/0144733 | A1 | 7/2003 | Brady et al. |
| 2005/0143812 | A1 | 6/2005 | Paul et al. |
| 2006/0115516 | A1 | 6/2006 | Pearson et al. |

FOREIGN PATENT DOCUMENTS

| | | | |
|---|---|---|---|
| EP | 161765 B1 | 10/1988 | |
| EP | 485197 A1 | 5/1992 | |
| EP | 488145 A2 | 6/1992 | |
| EP | 359829 B1 | 11/1993 | |
| EP | 1043365 A1 | 10/2000 | |
| EP | 1030194 B1 | 12/2002 | |
| EP | 1293541 A2 | 3/2003 | |
| FR | 2622984 A1 | 5/1989 | |
| JP | 1501172 T | 4/1989 | |
| JP | 1204668 A | 8/1989 | |
| JP | H06501794 A | 2/1994 | |
| JP | H06501795 A | 2/1994 | |
| JP | 6072151 A | 3/1994 | |
| JP | 6135985 A | 5/1994 | |
| JP | 6258604 A | 9/1994 | |
| JP | 6262861 A | 9/1994 | |
| JP | 6324293 A | 11/1994 | |
| JP | 7024052 A | 1/1995 | |
| JP | 7258166 A | 10/1995 | |
| JP | 8503997 T | 4/1996 | |
| JP | 9187500 A | 7/1997 | |
| JP | 10111641 A | 4/1998 | |
| JP | 10195324 A | 7/1998 | |
| JP | 2000007735 A | 1/2000 | |
| JP | 2002006268 A | 1/2002 | |
| JP | 2002514662 A | 5/2002 | |
| JP | 2003144538 A | 5/2003 | |
| JP | 2003144638 A | 5/2003 | |
| WO | WO8705712 A1 | 9/1987 | |
| WO | WO8802871 A1 | 4/1988 | |
| WO | WO8907952 A1 | 9/1989 | |
| WO | WO9511279 A1 | 4/1995 | |
| WO | WO9825173 A1 | 6/1998 | |
| WO | WO9825180 A1 | 6/1998 | |
| WO | WO9844380 A1 | 10/1998 | |
| WO | WO2005066694 A2 | 7/2005 | |

OTHER PUBLICATIONS

Miranda R., et al., "Mass Spectrometric Study of Benzylidenecyanoacetamides," Rapid Communiations in Mass Spectrometry, 1999, vol. 13 (1), pp. 33-38.

Office Action mailed Oct. 16, 2012 for Japanese Application No. 2007543134 filed Nov. 10, 2005.

Reddy T.I., et al., "Rare-earth (RE) Exchanged NaY Zeolite Promoted Knoevenagel Condensation," Tetrahedron Letters, 1997, vol. 38 (10), pp. 1721-1724.

Shiraishi T., et al., "Specific Inhibitors of Tyrosine-Specific Protein Kinase. I. Synthesis and Inhibitory Activities of Alpha-Cyanocinnamamides," Chemical and Pharmaceutical Bulletin, 1988, vol. 36 (3), pp. 974-981.

Wells G., et al., "Structural Studies on Bioactive Compounds. 32. Oxidation of Tyrphostin Protein Tyrosine Kinase Inhibitors with Hypervalent Iodine Reagents," Journal of Medicinal Chemistry, 2000, vol. 43 (8), pp. 1550-1562.

COPOLYMERIZABLE METHINE AND ANTHRAQUINONE COMPOUNDS AND ARTICLES CONTAINING THEM

CROSS REFERENCE TO RELATED APPLICATIONS

This application is a divisional of U.S. patent application Ser. No. 12/257,277, filed Oct. 23, 2008 now U.S. Pat. No. 8,360,576, which is a continuation of U.S. patent application Ser. No. 11/271,382 filed on Nov. 10, 2005, now abandoned, which claims the benefit of U.S. provisional patent application No. 60/629,556 filed Nov. 22, 2004, all aforementioned documents are incorporated herein by reference.

FIELD OF THE INVENTION

This invention relates to polymerizable ultraviolet light absorbers, yellow colorants and their use in ophthalmic lenses. In particular, this invention relates to polymerizable ultraviolet light absorbing methine compounds and polymerizable yellow compounds of the methine and anthraquinone classes that block ultraviolet light and/or violet-blue light transmission through ophthalmic lenses.

BACKGROUND OF THE INVENTION

The sun freely emits ultraviolet (UV), visible and infrared (IR) radiation, much of which is absorbed by the atmosphere. Solar radiation that is transmitted through the atmosphere and reaches the earth's surface includes UV-A radiation (320-400 nm), UV-B radiation (290-320 nm), visible light (400-700 nm) and near IR radiation (700-1400 nm). The ocular lens of humans in its normal, healthy state freely transmits near IR and most of the visible spectrum to the retina, but the lens acts to absorb UV radiation to avoid damage to the retina. The ability to absorb near UV and the violet-blue portion of the visible spectrum changes throughout life. In infancy, the human lens will freely transmit near UV and visible light above 300 nm, but with further aging the action of UV radiation from the environment causes the production of yellow colorants, fluorogens, within the lens. Some studies indicate that by age 54 the lens will not transmit light below 400 nm and the transmission of light between 400 and 450 nm is greatly diminished. As the lens ages it continuously develops a yellow color, increasing its capacity to filter out near UV and violet-blue light. Therefore, after cataract removal the natural protection provided by the aged human lens is also removed. Cataracts are typically replaced by an intraocular lens (IOL). If the brain is stimulated by signals caused by the visible light that has not been transmitted for many years, discomfort can result. Development of IOL materials with an absorption similar to aged human lens material would be a welcome improvement to the art.

Although yellow colorants exist, many such colorants are unsuitable for use in artificial lens material due to their tendency to leach out of the IOL after it is inserted in the eye or during solvent extraction associated with lens manufacture. A yellow colorant that is covalently bonded to lens materials would be thus be a desirable improvement in the manufacture of artificial lens materials. Efforts have been made to develop such a lens material. One obstacle of such efforts has been finding a polymerizable compound that will produce IOLs having an absorption profile that carefully matches that of the aged human lens, especially in the visible spectrum. If the IOL absorbs more than the lens in portions of the visible spectrum, visible acuity can be diminished. If the IOL absorbs less in the visible spectrum, the discomfort discussed above can result. Another obstacle that such efforts have faced has been the need to use a combination of multiple compounds to achieve a careful match with the human lens. Use of multiple compounds can result in a more complicated manufacturing process, along with increased production and materials costs. A polymerizable yellow colorant that matches the absorption spectra of the human lens and reduces the need for multiple colorants in an IOL would be a welcome improvement in the art.

More broadly, the development of yellow colorants and absorbers of ultraviolet light that can be covalently bonded to various polymeric materials would have numerous other uses beyond that in artificial lenses. For example, such colorants could be used with a wide array of polymeric applications in which the appropriate absorption spectrum is desired. Thus, what is needed in the art is novel yellow colorants and ultraviolet light absorbers (UVAs) that are more economical, and have spectral properties that better suit their target applications.

SUMMARY OF THE INVENTION

The invention solves the problems in the prior art by providing molecules that contain methine chromophores and/or anthraquinone chromophores and ethylenically-unsaturated polymerizable groups. These chromophores are present as structures that include at least one of the following moieties:

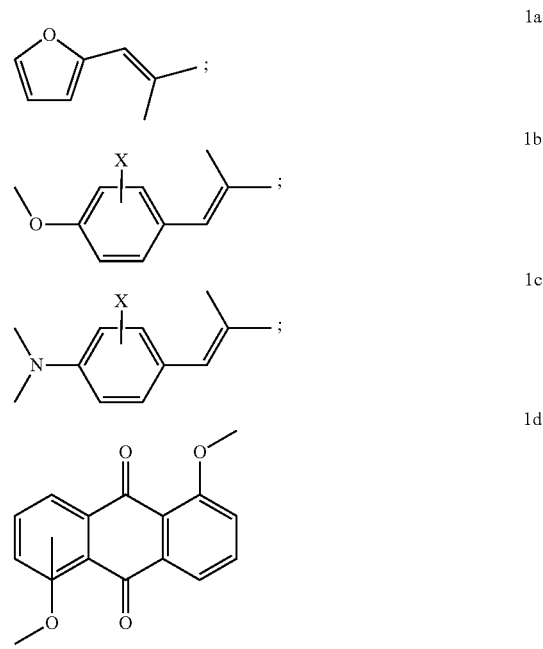

wherein X is selected from hydrogen or one or two groups selected from hydroxy, $C_1$-$C_6$ alkyl, $C_1$-$C_6$ alkoxy and halogen. The molecules of the present invention contain these moieties as well as at least one ethylenically-unsaturated polymerizable group that is capable of undergoing free radical polymerization without destroying the moiety. The ethylenically-unsaturated polymerizable group exists in addition to any such group that appears in the above figures. Thus, in the case of structure 1a, the resulting molecule contains at least one polymerizable ethylenically unsaturated group in addition to the ethylenically unsaturated group(s) depicted. It is to be understood that these moieties are only portions of the molecules and that the molecules contain additional moieties. Thus for example, in some embodiments the molecule of the present invention is one of the compounds represented by Formulae II-VI below:

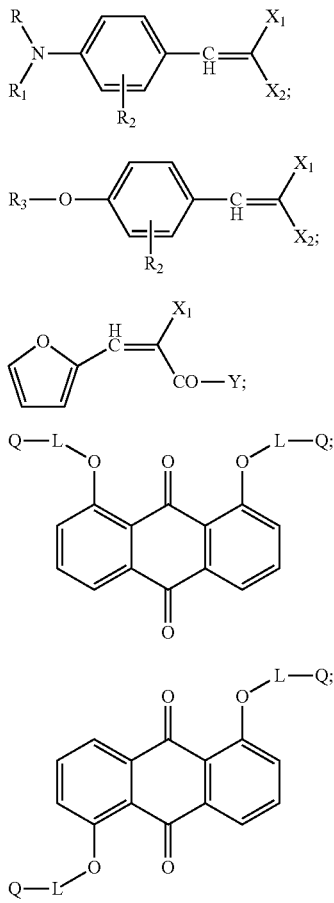

wherein:
R and $R_1$ are independently selected from $C_1$-$C_{12}$-alkyl, substituted $C_1$-$C_{12}$-alkyl, aryl, heteroaryl, $C_3$-$C_8$-cycloalkyl, $C_3$-$C_8$-alkenyl, —(CHR'CHR"O—)$_n$—$R_4$, $C_1$-$C_6$-alkylsulfonyl, arylsulfonyl, $C_1$-$C_{12}$-acyl, substituted-$C_1$-$C_{12}$-acyl, -L-Q and -Q; R and $R_1$ can be combined to make cyclic structures such as phthalimido, succinimido, morpholino, thiomorpholino, pyrrolidino, piperidino, piperazino, thiomorpholino-S,S-dioxide and the like;
n is an integer selected from 1 to about 1000;
$R_2$ is selected from hydrogen or one or two groups selected from hydroxy, $C_1$-$C_6$ alkyl, $C_1$-$C_6$ alkoxy and halogen;
$R_3$ is selected from hydrogen, $C_1$-$C_{12}$-alkyl, substituted $C_1$-$C_{12}$-alkyl, aryl, $C_3$-$C_8$-cycloalkyl, $C_3$-$C_8$-alkenyl and —(CHR'CHR"O—)$_n$—$R_4$, $C_1$-$C_{12}$-acyl, substituted-$C_1$-$C_{12}$-acyl, -L-Q and Q;
$R_4$ is selected from hydrogen, $C_1$-$C_{12}$-alkyl, $C_1$-$C_6$-alkanoyl and aryl;
R' and R" are independently selected from hydrogen and $C_1$-$C_{12}$-alkyl;
L is a divalent organic radical selected from $C_1$-$C_6$-alkylene-O—, $C_1$-$C_6$-alkylene-NR'—; arylene-$C_1$-$C_6$-alkylene-O—, arylene-$C_1$-$C_6$-alkylene-NR'—, arylene-O(CHR'CHR"O)$_n$—, $C_1$-$C_6$-alkylene-$Y_1$—(CHR'CHR"O—)$_n$—, —(CHR'CHR"O—)$_n$—;

Y is selected from —O-L-Q, —NR'-L-Q, —N-(L-Q)$_2$, —R$_5$;
$Y_1$ is selected from —O—, —S—, —SO$_2$—, —N(SO$_2$R$_5$)—, or —N(COR$_5$)—;
$R_5$ is $C_1$-$C_{12}$-alkyl, substituted $C_1$-$C_{12}$-alkyl, $C_3$-$C_8$-cycloalkyl or aryl;
$X_1$ and $X_2$ are independently selected from cyano, $C_1$-$C_6$-alkoxycarbonyl, $C_1$-$C_6$-alkylsulfonyl, arylsulfonyl, carbamoyl, $C_1$-$C_6$-alkanoyl, aroyl, aryl, heteroaryl and —COY;
Q is a group that includes an ethylenically-unsaturated polymerizable group;
wherein the compound comprises or has bonded thereto at least one Q group.

As can be seen, Formula II depicts a molecule containing moiety 1c. Formula III depicts a molecule containing moiety 1b. Formula IV depicts a molecule containing moiety 1a. Formulae V and VI depict molecules containing moiety 1d.

It will be understood that the location of atoms bonded to the carbons in any ethene double bond in Formulas II, III, and IV should not be interpreted as limiting and that Formulas II, III, and IV should be interpreted as including both cis and trans stereoisomers throughout this application, including the claims.

In some embodiments, the compounds of the present invention are polymerized with other molecules capable of polymerizing to form a polymer in which the compounds are part of the backbone. In some embodiments, the compounds are polymerized with organic monomers to form a material that is transparent to visible light, or that has a degree of absorption or transparency to various light wavelengths that mimics that of a desired material, such as the lens of a mammalian eye of a given age. However, the invention includes all types of polymers irrespective of the degree of transparency, translucency, or opacity to any type of radiation.

By bonding the compound to the polymer, the potential for the compound leaching out of the material is diminished or eliminated. As a result, in some embodiments these compounds are used in transparent materials to decrease the intensity of violet-blue light transmitted through them. These transparent materials with one or more of the bondable yellow compounds and/or bondable UVAs incorporated in them may be extracted with organic solvents to remove unreacted monomers, low molecular weight oligomers and low molecular weight polymers, as well as other impurities, and then used to make ocular lenses such as intraocular lenses (IOLs), contact lenses, eyeglasses and other windows. These transparent materials containing yellow compounds may also be used to make lens coating materials. Surprisingly, the methine chromophores of the present invention do not lose their absorbance properties upon free radical polymerization. This is surprising since the chromophoric unit is an ethylenically unsaturated moiety so that the polymerization reaction involving the chromophoric unit would be expected to result in loss of the absorption properties.

Thus, the invention includes the compounds disclosed herein.

The invention further includes compositions comprising the compounds of the present invention. In some embodiments, the compositions are polymerizable compositions.

The invention further includes methods of making a polymer comprising polymerizing a group of monomers, prepolymers, chain extenders, or combinations of thereof, one or more of which contains a compound of the present invention or a residue of such a compound.

The invention further includes polymers that contain the residue of the polymerization of the compounds of the present invention.

The invention further includes articles that contain the polymers of the present invention. In some embodiments, the articles are transparent. In some embodiments, the articles are optical objects. In some embodiments, the articles are IOLs.

DETAILED DESCRIPTION OF THE INVENTION

Polymerizable yellow compounds and UV absorbing compounds that are based on the methine and anthraquinone chromophores and contain polymerizable, ethylenically unsaturated moieties are provided. The invention further includes compositions comprising the compounds of the present invention. In some embodiments, the compositions are polymerizable compositions. The invention further includes methods of making a polymer comprising polymerizing a group of monomers, prepolymers, chain extenders, or combinations of thereof, one or more of which contains a compound of the present invention or a residue of such a compound. The invention further includes polymers that contain the residue of the polymerization of the compounds of the present invention. The invention further includes articles that contain the polymers of the present invention. In some embodiments, the articles are transparent. In some embodiments, the articles are optical objects. In some embodiments, the articles are IOLs.

DEFINITIONS

The following definitions apply to terms as used throughout this application.

The term "chromophoric unit" means the portion of a molecule primarily responsible for causing the absorption of radiation at the wavelength of maximum absorption.

The alkyl groups described by the terms "$C_1$-$C_6$-alkyl" and "$C_1$-$C_6$ alkoxy" refer to straight or branched chain hydrocarbon radicals containing one to six carbon atoms optionally substituted with hydroxy, cyano, aryl, —$OC_1$-$C_4$-alkyl, —$OCOC_1$-$C_4$-alkyl and —$CO_2C_1$-$C_4$-alkyl, wherein the $C_1$-$C_4$-alkyl portion of the groups represents a saturated straight or branched chain hydrocarbon radical that contains one to four carbon atoms.

The alkyl groups described by the term "$C_1$-$C_{12}$-alkyl" refer to straight or branched chain hydrocarbon radicals containing one to twelve carbon atoms.

The terms "$C_1$-$C_{12}$-acyl" and "substituted-$C_1$-$C_{12}$-acyl" are used to represent —CO—($C_1$-$C_{12}$-alkyl) and —CO-(substituted $C_1$-$C_{12}$-alkyl), respectively.

The term "$C_3$-$C_8$-cycloalkyl" refers to a cyclic hydrocarbon radical containing three to eight carbon atoms.

The term "aryl" includes phenyl and naphthyl and these radicals substituted with one to three $C_1$-$C_6$-alkyl, $C_1$-$C_6$-alkoxy, —CN, —$NO_2$, $C_1$-$C_6$-alkoxycarbonyl, $C_1$-$C_6$-alkanoyloxy, $C_1$-$C_6$— alkylsulfonyl, hydroxyl, carboxy or halogen groups.

The term "heteroaryl" includes 5 or 6-membered heterocyclic aryl rings containing one oxygen atom, and/or one sulfur atom, and up to three nitrogen atoms, said heterocyclic aryl ring optionally fused to one or two phenyl rings. Examples of such systems include thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, tetrazolo-[1,5-b]pyridazinyl and purinyl, benzoxazolyl, benzothiazolyl, benzimidazolyl, indolyl and the like; these are optionally substituted with one to three $C_1$-$C_6$-alkyl, aryl, $C_1$-$C_6$-alkoxy, —CN, —$NO_2$, $C_1$-$C_6$-alkoxycarbonyl, $C_1$-$C_6$-alkanoyloxy, $C_1$-$C_6$-alkylsulfonyl or halogen groups.

The term "substituted-$C_1$-$C_{12}$-alkyl" is used herein to denote a straight or branched chain, saturated aliphatic hydrocarbon radical containing one to twelve carbon atoms and these radicals optionally substituted with one to three groups selected from hydroxy; halogen; cyano; succinimido; glutarimido; phthalimido; 2-pyrrolidono; aryl; heteroaryl; heteroarylthio; aryloxy; arylthio; $C_1$-$C_6$-alkoxy, $C_1$-$C_6$-alkylthio; $C_1$-$C_6$-alkylsulfonyl; arylsulfonyl; sulfamyl; benzoylsulfonicimido; $C_1$-$C_6$-alkylsulfonamido; arylsulfonamido; $C_3$-$C_8$-alkenylcarbonylamino; —NR'-L-Q; —N-(L-Q)$_2$; —O-L-Q; groups of the formula

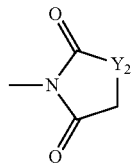

wherein $Y_2$ is —NH—, —N($C_1$-$C_{12}$-alkyl)-, —O—, —S—, or —$CH_2O$—; —$OX_3R_{12}$, —$NHX_3R_{12}$; —$CONR_{13}R'_{13}$; —$SO_2NR_{13}R'_{13}$; wherein $R_{12}$ is selected from $C_1$-$C_{12}$-alkyl and $C_1$-$C_6$-alkyl substituted with halogen, phenoxy, aryl, cyano, $C_3$-$C_8$-cycloalkyl, $C_1$-$C_6$-alkylsulfonyl, $C_1$-$C_6$-alkylthio, and $C_1$-$C_6$-alkoxy; $R_{13}$ and $R'_{13}$ are independently selected from hydrogen, aryl, $C_1$-$C_{12}$-alkyl and $C_1$-$C_6$-alkyl substituted with halogen, phenoxy, aryl, —CN, cyclolalkyl, $C_1$-$C_6$-alkylsulfonyl, $C_1$-$C_6$-alkylthio, or $C_1$-$C_6$-alkoxy; $X_3$ is selected from —CO—, —COO—, —CONH—, or —$SO_2$—; $C_3$-$C_8$-cycloalklyl; $C_1$-$C_6$-alkanoyloxy; $C_1$-$C_6$-alkoxycarbonyl and —(O—$C_2$-$C_4$-alkylene)$_nR_{14}$; wherein $R_{14}$ is selected from hydrogen, $C_1$-$C_6$-alkoxy, halogen, hydroxy, cyano, $C_1$-$C_6$-alkanoyloxy, $C_1$-$C_6$-alkoxycarbonyl, aryl, $C_3$-$C_8$-cycloalkyl; and —OQ; n is as previously defined.

The term "$C_1$-$C_6$-alkylene" refers to a straight or branched chain, divalent hydrocarbon radical containing one to six carbon atoms and optionally substituted with hydroxy, halogen, aryl, $C_1$-$C_6$-alkanoyloxy, or —OQ.

The term "halogen" means any of the following atoms: fluorine, chlorine, bromine and iodine.

The terms "$C_1$-$C_6$-alkoxycarbonyl" and "$C_1$-$C_6$-alkanoyloxy" denote the radicals —$CO_2C_1$-$C_6$-alkyl and —O—$COC_1$-$C_6$-alkyl, respectively.

The term "$C_3$-$C_8$ alkenyl" denotes a straight or branched chain hydrocarbon radical that contains at least one carbon-carbon double bond.

In the terms "arylsulfonyl" and "aroyl" the aryl groups or aryl portions of the groups are selected from phenyl and naphthyl, and these may optionally be substituted with hydroxy, halogen, carboxy, $C_1$-$C_6$-alkyl, $C_1$-$C_6$-alkoxy and $C_1$-$C_6$-alkoxycarbonyl.

The term "carbamoyl" is used to represent the group having the formula: —CON($R_{15}$)$R_{16}$, wherein $R_{15}$ and $R_{16}$ are selected from hydrogen, $C_1$-$C_6$-alkyl, $C_3$-$C_8$-cycloalkyl, $C_3$-$C_8$-alkenyl, and aryl.

The term "$C_1$-$C_6$-alkylsulfonyl" is used to represent —$SO_2$—$C_1$-$C_6$-alkyl wherein the term "$C_1$-$C_6$-alkyl" is as previously defined.

References herein to groups or moieties having a stated range of carbon atoms, such as "$C_1$-$C_6$-alkyl," shall mean not only the $C_1$ group (methyl) and $C_6$ group (hexyl) end points, but also each of the corresponding individual $C_2$, $C_3$, $C_4$ and $C_5$ groups. In addition, it will be understood that each of the individual points within a stated range of carbon atoms may be further combined to describe subranges that are inherently within the stated overall range. For example, the term "$C_3$-$C_8$-cycloalkyl" includes not only the individual cyclic moieties $C_3$ through $C_8$, but also contemplates subranges such as "$C_4$-$C_6$-cycloalkyl."

The phrase "ethylenically-unsaturated polymerizable group" and/or "free radical initiated polymerizable group" shall mean a moiety having a C=C double bond that is reactive in a free radical polymerization, including but not limited to those having a vinyl group. In some embodiments, the reactive double bond is activated by one of the double-bonded carbons being attached to an aryl group or an electron withdrawing group such as a carbonyl. Although aromatic and heteroaromatic rings are often drawn in this application and elsewhere in a way that depicts the aromatic pi cloud of electrons in such rings as alternating double bonds (for example, benzene is often drawn as a six membered ring containing three alternating double and single bonds) the skilled artisan will understand that such rings do not actually contain double bonds but instead contain an aromatic pi cloud of completely delocalized electrons and, as such, are unreactive to free radical polymerization. Accordingly, none of the terms "reactive C=C double bond," "ethylenically-unsaturated polymerizable group," and "free radical initiated polymerizable group" include aromatic pi clouds of electrons in aromatic or heteroaromatic ring, irrespective of whether such aromatic pi clouds of electrons are representing in any drawing as alternating double bonds.

Compounds

The compounds are molecules that include at least one of the following moieties:

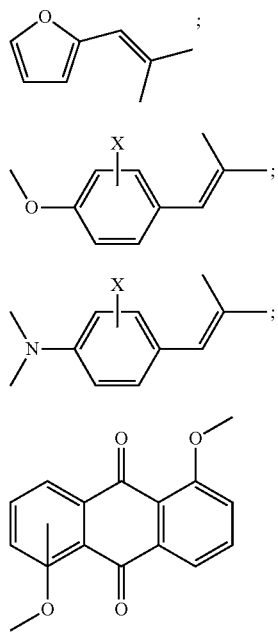

wherein X is selected from hydrogen or one or two groups selected from hydroxy, $C_1$-$C_6$ alkyl, $C_1$-$C_6$ alkoxy and halogen. The molecules of the present invention contain these moieties as well as at least one ethylenically-unsaturated polymerizable group that is capable of undergoing free radical polymerization without destroying the moiety. The ethylenically-unsaturated polymerizable group exists in addition to any such group that appears in the above figures. Thus, in the case of structure 1a, the resulting molecule contains at least one polymerizable ethylenically unsaturated group in addition to the ethylenically unsaturated group(s) depicted. It is to be understood that these moieties are only portions of the molecules and that the molecules contain additional moieties. Thus, for example, in some embodiments the molecule of the present invention is one of the compounds represented by Formulae II-VI below:

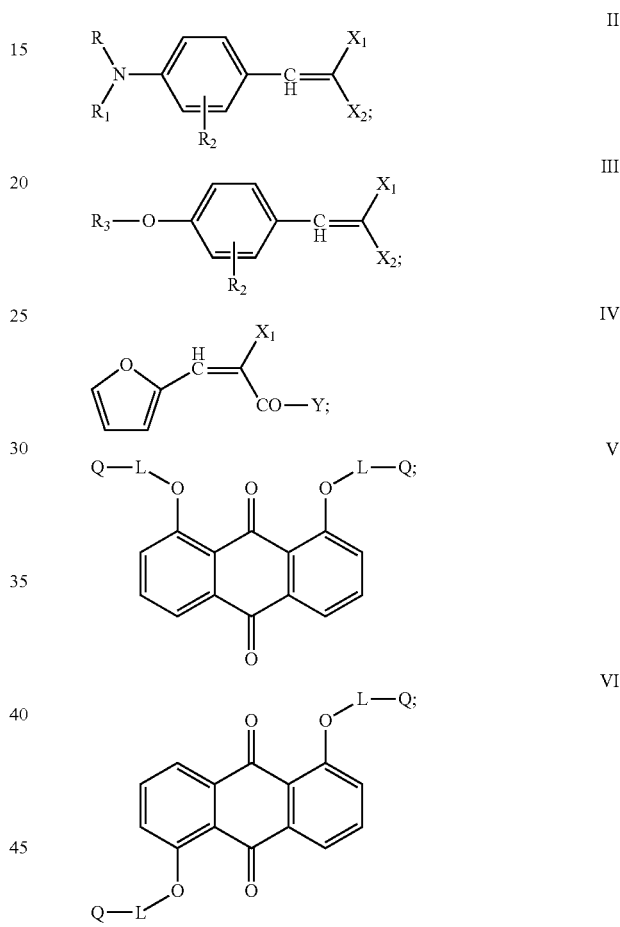

wherein:
R and $R_1$ are independently selected from $C_1$-$C_{12}$-alkyl, substituted $C_1$-$C_{12}$-alkyl, aryl, heteroaryl, $C_3$-$C_8$-cycloalkyl, $C_3$-$C_8$-alkenyl, —(CHR'CHR"O—)$_n$—R$_4$, $C_1$-$C_6$-alkylsulfonyl, arylsulfonyl, $C_1$-$C_{12}$-acyl, substituted-$C_1$-$C_{12}$-acyl, -L-Q and -Q; R and $R_1$ can be combined to make cyclic structures such as phthalimido, succinimido, morpholino, thiomorpholino, pyrrolidino, piperidino, piperazino, thiomorpholino-S,S-dioxide and the like;
n is an integer selected from 1 to about 1000;
$R_2$ is selected from hydrogen or one or two groups selected from hydroxy, $C_1$-$C_6$ alkyl, $C_1$-$C_6$ alkoxy and halogen;
$R_3$ is selected from hydrogen, $C_1$-$C_{12}$-alkyl, substituted $C_1$-$C_{12}$-alkyl, aryl, $C_3$-$C_8$-cycloalkyl, $C_3$-$C_8$-alkenyl and —(CHR'CHR"O—)$_n$—R$_4$, $C_1$-$C_{12}$-acyl, substituted-$C_1$-$C_{12}$-acyl, -L-Q and Q;
$R_4$ is selected from hydrogen, $C_1$-$C_{12}$-alkyl, $C_1$-$C_6$-alkanoyl and aryl;

R' and R" are independently selected from hydrogen and $C_1$-$C_{12}$-alkyl;

L is a divalent organic radical selected from $C_1$-$C_6$-alkylene-O—, $C_1$-$C_6$-alkylene-NR—; arylene-$C_1$-$C_6$-alkylene-O—, arylene-$C_1$-$C_6$-alkylene-NR—, arylene-O(CHR'CHR"O)$_n$—, $C_1$-$C_6$-alkylene-$Y_1$—(CHR'CHR"O—)$_n$—, —(CHR'CHR"O—)$_n$—;

Y is selected from —O-L-Q, —NR'-L-Q, —N-(L-Q)$_2$, —$R_5$;

$Y_1$ is selected from —O—, —S—, —SO$_2$—, —N(SO$_2$R$_5$)—, or —N(COR$_5$)—;

$R_5$ is $C_1$-$C_{12}$-alkyl, substituted $C_1$-$C_{12}$-alkyl, $C_3$-$C_8$-cycloalkyl or aryl;

$X_1$ and $X_2$ are independently selected from cyano, $C_1$-$C_6$-alkoxycarbonyl, $C_1$-$C_6$-alkylsulfonyl, arylsulfonyl, carbamoyl, $C_1$-$C_6$-alkanoyl, aroyl, aryl, heteroaryl and —COY;

Q is a group that includes an ethylenically-unsaturated polymerizable group;

wherein the compound includes at least one Q group.

As can be seen, Formula II depicts examples of a molecule containing moiety 1c. Formula III depicts examples of a molecule containing moiety 1b. Formula IV depicts examples of a molecule containing moiety 1a. Formulae V and VI depict examples of molecules containing moiety 1d.

It will be understood that the location of atoms bonded to the carbons in any ethene double bond in Formulas II, III, and IV should not be interpreted as limiting and that Formulas II, III, and IV should be interpreted as including both cis and trans stereoisomers throughout this application, including the claims.

In some embodiments, the alkoxylated moiety of R, $R_1$, $R_3$ and L include either ethylene oxide or propylene oxide, or mixtures of both, thereon having a chain length denoted by the formula wherein n is from 1 to about 100. In some embodiments, the chain length is denoted by the formula wherein n is less than 50. In some embodiments, the chain length is denoted by the formula wherein n is less than about 8.

Examples of Q groups include but are not limited to the following organic radicals 1-9:

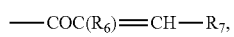 (a)

 (b)

 (c)

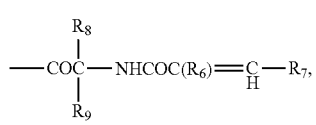 (d)

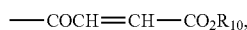 (e)

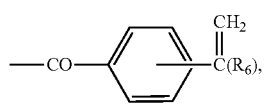 (f)

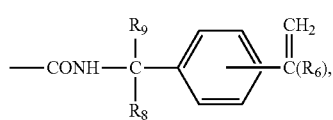 (g)

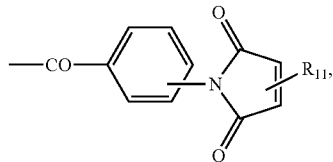 (h)

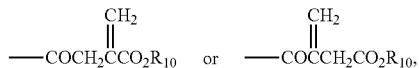 (i)

or a combination of the two structures on a plurality of compounds;

wherein:

$R_6$ is hydrogen or $C_1$-$C_6$-alkyl;

$R_7$ is: hydrogen; $C_1$-$C_6$ alkyl; phenyl; phenyl substituted with one or more groups selected from $C_1$-$C_6$-alkyl, $C_1$-$C_6$-alkoxy, —N($C_1$-$C_6$-alkyl)$_2$, nitro, cyano, $C_1$-$C_6$-alkoxycarbonyl, $C_1$-$C_6$-alkanoyloxy and halogen; 1- or 2-naphthyl; 1- or 2-naphthyl substituted with $C_1$-$C_6$-alkyl or $C_1$-$C_6$-alkoxy; 2- or 3-thienyl; 2- or 3-thienyl substituted with $C_1$-$C_6$-alkyl or halogen; 2- or 3-furyl; or 2- or 3-furyl substituted with $C_1$-$C_6$-alkyl;

$R_8$ and $R_9$ are, independently, hydrogen, $C_1$-$C_6$-alkyl, or aryl; or $R_8$ and $R_9$ are combined to form a —(CH$_2$)$_{3-5}$ radical;

$R_{10}$ is hydrogen, $C_1$-$C_6$-alkyl, $C_1$-$C_8$-alkenyl, $C_3$-$C_8$-cycloalkyl or aryl; and $R_{11}$ is hydrogen, $C_1$-$C_6$-alkyl or aryl.

In some embodiments, a compound of Formulae II, III, IV, V or VI is used in which Q is

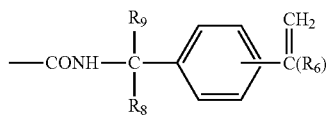

wherein $R_6$ is hydrogen or methyl and $R_8$ and $R_9$ are methyl.

In some embodiments, a compound of Formulae II, III, IV, V or VI is used in which Q is:

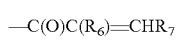

wherein $R_6$ is hydrogen or methyl; and $R_7$ is hydrogen.

In some embodiments compound has a structural formula consistent with Formula II in which: R and $R_1$ are independently selected from $C_1$-$C_{12}$-alkyl, substituted $C_1$-$C_{12}$-alkyl, aryl, heteroaryl, $C_3$-$C_8$-cycloalkyl, $C_3$-$C_8$-alkenyl, —(CHR'CHR"O—)$_n$—$R_4$, $C_1$-$C_6$-alkylsulfonyl, arylsulfonyl, $C_1$-$C_{12}$-acyl, substituted-$C_1$-$C_{12}$-acyl, -L-Q and -Q; R and $R_1$ can be combined to make cyclic structures such as phthalimido, succinimido, morpholino, thiomorpholino, pyrrolidino, piperidino, piperazino, thiomorpholino-S,S-dioxide and the like;

n is an integer selected from 1 to about 1000;

$R_2$ is selected from hydrogen or one or two groups selected from hydroxy, $C_1$-$C_6$ alkyl, $C_1$-$C_6$ alkoxy and halogen;

R' and R" are independently selected from hydrogen and $C_1$-$C_{12}$-alkyl;

L is a divalent organic radical selected from $C_1$-$C_6$-alkylene-O—, $C_1$-$C_6$-alkylene-NR—; arylene-$C_1$-$C_6$-alkylene-O—, arylene-$C_1$-$C_6$-alkylene-NR—, arylene-O(CHR'CHR"O)$_n$—, $C_1$-$C_6$-alkylene-$Y_1$—(CHR'CHR"O—)$_n$—, —(CHR'CHR"O—)$_n$—;

Y is selected from —O-L-Q, —NR'-L-Q, —N-(L-Q)$_2$, —R$_5$;
Y$_1$ is selected from —O—, —S—, —SO$_2$—, —N(SO$_2$R$_5$)—, or —N(COR$_5$)—;
R$_4$ is selected from hydrogen, C$_1$-C$_{12}$-alkyl, C$_1$-C$_6$-alkanoyl and aryl;
R$_5$ is C$_1$-C$_{12}$-alkyl, substituted C$_1$-C$_{12}$-alkyl, C$_3$-C$_8$-cycloalkyl or aryl;
X$_1$ and X$_2$ are independently selected from cyano, —CO$_2$C$_1$-C$_6$-alkyl, C$_1$-C$_6$-alkylsulfonyl, arylsulfonyl, carbamoyl, C$_1$-C$_6$-alkanoyl, aroyl, aryl, heteroaryl and —COY;
Q is a group that includes an ethylenically-unsaturated polymerizable group; the compound comprises or has bonded thereto at least one Q group.

In some embodiments the compound is a compound of Formula II wherein R and R$_1$ are independently selected from —CH$_2$CH$_2$CN, —CH$_2$CH$_2$Cl, —CH$_2$CH$_2$—OCO—C$_1$-C$_4$-alkyl, —CH$_2$CH$_2$OCO-aryl, —CH$_2$CH$_2$—OC(O)NH-aryl, —C$_1$-C$_4$-alkyl, —CH$_2$C$_6$H$_4$CO$_2$—C$_1$-C$_4$-alkyl,

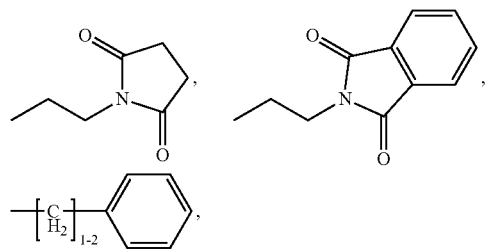

or combined to make the cyclic structure thiomorpholino-S, S-dioxide;
Y is —NH-L-Q; L is —CH$_2$CH$_2$O—, —CH$_2$CH(CH$_3$)O—, —(CH$_2$)$_3$O—, —(CH$_2$)$_4$O—, —(CH$_2$)$_6$O—, —CH$_2$C(CH$_3$)$_2$CH$_2$O—, —CH$_2$—C$_6$H$_{10}$—CH$_2$O—, —C$_6$H$_4$CH$_2$CH$_2$O—, —C$_6$H$_4$—OCH$_2$CH$_2$O—, —CH$_2$CH$_2$(OCH$_2$CH$_2$)$_{1-3}$O—, and
Q is

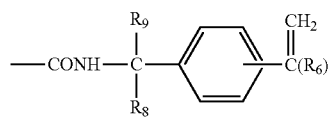

wherein R$_6$ is methyl; R$_8$ and R$_9$ are methyl.

In some embodiments the compound is a compound of Formula II wherein R and R$_1$ are independently selected from —CH$_2$CH$_2$CN, —CH$_2$CH$_2$Cl, —CH$_2$CH$_2$—OCO—C$_1$-C$_4$-alkyl, —CH$_2$CH$_2$OCO-aryl, —CH$_2$CH$_2$—OC(O)NH-aryl, —C$_1$-C$_4$-alkyl, —CH$_2$C$_6$H$_4$CO$_2$—C$_1$-C$_4$-alkyl,

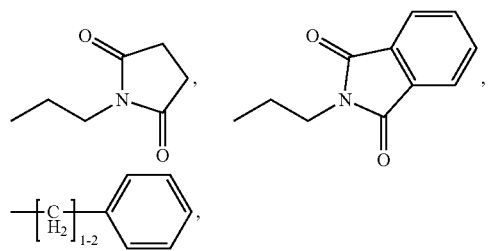

or combined to make the cyclic structure thiomorpholino-S, S-dioxide; Y is —NH-L-Q; L is —CH$_2$CH$_2$O—, —CH$_2$CH(CH$_3$)O—, —(CH$_2$)$_3$O—, —(CH$_2$)$_4$O—, —(CH$_2$)$_6$O—, —CH$_2$C(CH$_3$)$_2$CH$_2$O—, —CH$_2$—C$_6$H$_{10}$—CH$_2$O—, —C$_6$H$_4$—CH$_2$CH$_2$O—, —C$_6$H$_4$—OCH$_2$CH$_2$O—, —CH$_2$CH$_2$(OCH$_2$CH$_2$)$_{1-3}$O—, and Q is:

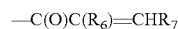

—C(O)C(R$_6$)=CHR$_7$ wherein R$_6$ is methyl; and R$_7$ is hydrogen.

In some embodiments the compound is a compound of Formula II wherein R is selected from —CH$_2$CH$_2$CN; wherein R$_1$ is selected from —CH$_2$CH$_2$CN, —CH$_2$CH$_2$Cl, —CH$_2$CH$_2$OCO—C$_1$-C$_4$-alkyl,

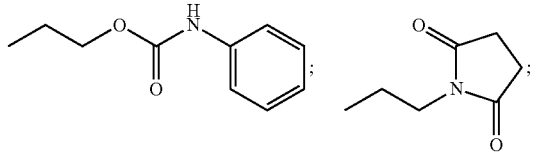

Y is —NH-L-Q; L is —CH$_2$CH$_2$O—, —CH$_2$CH(CH$_3$)O—, and Q is

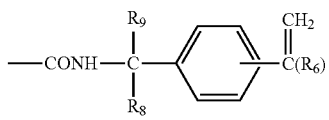

wherein R$_6$ is methyl; R$_8$ and R$_9$ are methyl.

In some embodiments the compound is a compound of Formula II wherein R is selected from —CH$_2$CH$_2$CN; wherein R$_1$ is selected from —CH$_2$CH$_2$CN, —CH$_2$CH$_2$Cl, —CH$_2$CH$_2$OCO—C$_1$-C$_4$-alkyl,

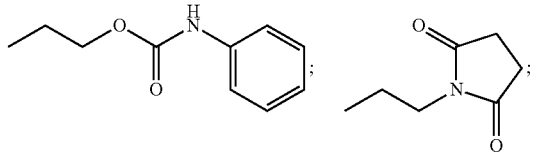

Y is —NH-L-Q; L is —CH$_2$CH$_2$O—, —CH$_2$CH(CH$_3$)O—, and Q is:

—C(O)C(R$_6$)=CHR$_7$ wherein R$_6$ is methyl; and R$_7$ is hydrogen.

In some embodiments, the compounds of the present invention have an maximum absorption less than 420 nm and have little if any absorption at wavelengths greater than about 450 nm at concentrations that are suitable in the present invention. In some embodiments, the wavelength at which maximum absorption occurs is between about 300 nm and about 420 nm. In some embodiments, there is minimal absorption at 450 nm. In some embodiments, the wavelength of maximum absorption is between about 350 nm and about 390 nm. In some embodiments, the wavelength of maximum absorption is between about 370 nm and about 380 nm. In some embodiments, the wavelength of maximum absorption of the ultraviolet light absorber is between about 310 nm and about 375 nm. In some embodiments, the wavelength of maximum absorption the absorption of the chromophoric unit at wavelength greater than 400 nm is no more than 20 percent of total absorption between about 330 nm and 450 nm.

Compositions Comprising the Compounds

Compositions comprising the compounds of the present invention are also provided. The compound may be incorporated in a number of materials in a variety of applications where it is desirable to achieve certain desired colors or desired wavelength absorbances.

In some embodiments, the composition is a polymerizable composition containing the compounds of the present invention. In some embodiments, the polymerizable composition contains an ultraviolet light absorbing methine polymerizable compound in combination with a yellow methine polymerizable compound and/or an anthraquinone polymerizable compound to obtain the correct shade of yellow while absorbing ultraviolet light in the wavelength range of 300 nm to 400 nm. The amount of yellow compound will be determined by the application and the spectral properties of the compound. The amount of yellow polymerizable compound may be determined by the thickness of the films (or lens) and by the practitioner. In some embodiments, the amount of yellow polymerizable compound is less than about 4 weight percent based upon the total weight of the resulting polymer. In some embodiments, the amount of yellow polymerizable compound is less than about 4 weight percent based upon the total weight of the resulting polymer. In some embodiments, the amount of yellow polymerizable compound is less than about 2 weight percent based upon the total weight of the resulting polymer. In some embodiments, the amount of yellow polymerizable compound is less than about 1.5 weight percent resulting polymer resulting polymer based upon the total weight of the resulting polymer. In some embodiments, the amount of yellow polymerizable compound is less than about 1 weight percent based upon the total weight of the resulting polymer. The ultraviolet light absorbing methine polymerizable compound will be added in sufficient amount to block the desired amount of ultraviolet light that penetrates the polymer, which is determined by the thickness of the film and the practitioner. In some embodiments, the amount of ultraviolet light absorbing polymerizable methine compound is less than about 4 weight percent based upon the total weight of the resulting polymer. In some embodiments, the amount of ultraviolet light absorbing polyermizable methine compound is less than about 2 weight percent based upon the total weight of the resulting polymer. In some embodiments, the amount of ultraviolet light absorbing polyermizable methine compound is less than about 1.5 weight percent based upon the total weight of the resulting polymer. In some embodiments, the amount of ultraviolet light absorbing polyermizable methine compound is less than about 1 weight percent based upon the total weight of the resulting polymer. The weight percentages in this paragraph are determined by dividing the weight of compound used in the polymerization by the total weight of the resulting polymer (multiplied by 100 percent).

In some embodiments, the polymerizable composition contains other ultra-violet absorbing compounds in addition to the compounds of the present invention. The ultraviolet absorbing material can be any compound which absorbs light having a wavelength shorter than about 400 nm but does not absorb any substantial amount of visible light. In some embodiments, the ultraviolet absorbing compound is incorporated into the monomer mixture and is entrapped in the polymer matrix when the monomer mixture is polymerized. Suitable ultraviolet absorbing compounds include substituted benzophenones, such as 2-hydroxybenzophenone, and 2-(2-hydroxyphenyl)benzotriazoles. In some embodiments, an ultraviolet absorbing compound which is copolymerizable with the monomers and is thereby covalently bound to the polymer matrix is used. In this way, the risk of leaching of the ultraviolet absorbing compound out of the lens and into the interior of the eye is reduced. Suitable copolymerizable ultraviolet absorbing compounds are the substituted 2-hydroxybenzophenones disclosed in U.S. Pat. No. 4,304,895 and the 2-hydroxy-5-acryloxyphenyl-2H-benzotriazoles disclosed in U.S. Pat. No. 4,528,311. In some embodiments, the ultraviolet absorbing compound 2-(3'-methallyl-2'-hydroxy-5'methyl phenyl)benzotriazole, also known as ortho-methallyl Tinuvin P ("oMTP") is included in the polymerizable composition. Any and all combinations of the other components in the polymerizable composition may be used.

Since some ultraviolet absorbing compounds have phenolic substituents or residues within their structure that are known to inhibit polymerization, it is sometimes advantageous to minimize the amount of ultraviolet absorbing compound in the polymerizable composition. Reducing the concentration of such ultraviolet absorbing compounds can be beneficial to the lens forming process. In some embodiments involving oMTP, that compound is present in a concentration of approximately 1.8 wt. %. However, depending on the specific yellow compound chosen and the desired transmission at a given wavelength, considerably less than 1.8 wt. % of oMTP may be used. In some embodiments, the ultraviolet light absorbing polymerizable compounds are represented by Formula III wherein $R_3$ is selected from substituted $C_1$-$C_{12}$-alkyl and -LQ; $R_2$ is selected from hydrogen, $C_1$-$C_6$-alkyl, and $C_1$-$C_6$-alkyoxy; $X_1$ is cyano; $X_2$ is selected from —$CO_2$—$C_1$-$C_6$-alkyl, —CONH—$C_1$-$C_6$-alkyl, —CN, —CONH-L-Q; L is —$CH_2CH_2O$—, —$CH_2CH(CH_3)O$—, —$(CH_2)_3$—, —$(CH_2)_4$—, —$(CH_2)_6$—, —$CH_2C(CH_3)_2CH_2$—, —$CH_2$—$C_6H_{10}$—$CH_2$—, —$C_6H_4$—$CH_2CH_2$—, —$C_6H_4$—$OCH_2CH_2$—, —$CH_2CH_2(OCH_2CH_2)_{1-3}$— and Q is

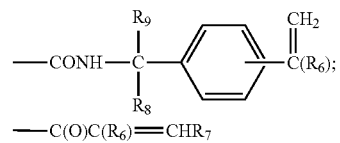

—C(O)C($R_6$)=CH$R_7$ wherein R' is selected from hydrogen or methyl; $R_6$ is methyl; $R_7$ is hydrogen and $R_8$ and $R_9$ are methyl. In some embodiments, the ultraviolet light absorbing polymerizable compounds do not contain phenolic moieties within their structure and are therefore have less of a detrimental effect on polymerization rates as compared to oMTP or other phenolic ultraviolet light absorbing compounds.

In some embodiments, the polymerizable composition includes a single component polymerizable methine or polymerizable anthraquinone compound that absorbs UV light having a wavelength from 350 nm to 400 nm and also absorbs the blue-violet light with wavelengths less than about 425 nm or by mixing a co-polymerizable methine UV absorber having a wavelength of maximum absorption of less than about 380 nm and a co-polymerizable yellow compound having a wavelength of maximum absorption of between 380 nm and 425 nm to achieve the desired absorption.

In some embodiments, the polymerizable composition contains other monomers that contain ethylenically-unsaturated polymerizable group. Any monomers that will polymerize with the compounds of the present invention can be used, including but not limited to hydrogel-forming polymers as well as vinyl-containing monomers such as acrylic, acrylate and/or methacrylate-based monomers. Examples of monomers used in some embodiments include but are not limited to: acrylic acid, methacrylic acid and their anhydrides; crotonic acid; crotonate esters; itaconic acid as well as its anhydride; cyanoacrylic acid as well as its esters; esters of acrylic and methacrylic acids such as allyl, methyl, ethyl, n-propyl, isopropyl, butyl, tetrahydrofurfuryl, cyclohexyl, isobornyl, n-hexyl, n-octyl, isooctyl, 2-ethylhexyl, lauryl, stearyl, and benzyl acrylate and methacrylate; hydroxyethyl acrylate and methacrylate; diacrylate and dimethacrylate esters of ethylene and propylene glycols, 1,3-butylene glycol, 1,4-butanediol, diethylene and dipropylene glycols, triethylene and tripropylene glycols, 1,6-hexanediol, neopentyl glycol, polyethylene glycol, and polypropylene glycol, ethoxylated bisphenol A, ethoxylated and propoxylated neopentyl glycol; triacrylate and trimethacrylate esters of tris-(2-hydroxyethyl) isocyanurate, trimethylolpropane, ethoxylated and propoxylated trimethylolpropane, pentaerythritol, glycerol, ethoxylated and propoxylated glycerol; tetraacrylate and tetramethacrylate esters of pentaerythritol and ethoxylated and propoxylated pentaerythritol; acrylonitrile; vinyl acetate; vinyl toluene; styrene; N-vinyl pyrrolidinone; alpha-methylstyrene; maleate/fumarate esters; maleic/fumaric acid; 1,6 hexanediol di(meth)acrylate; neopentyl glycol diacrylate; methacrylate; vinyl ethers; divinyl ethers such as diethyleneglycol divinyl ether, 1,6-hexanediol divinyl ether, cyclohexanedimethanol divinyl ether, 1,4-butanediol divinyl ether, triethyleneglycol divinyl ether, trimethylolpropane divinyl ether, and neopentyl glycol divinyl ether, vinyl esters; divinyl esters such as divinyl adipate, divinyl succinate, divinyl glutarate, divinyl 1,4-cyclohexanedicarboxylate, divinyl 1,3-cyclohexanedicarboxylate, divinyl isophthalate, and divinyl terephthalate; N-vinyl pyrrolidone; tetraethylene glycol dimethacrylate; allyl acrylate; allyl methacrylate; trifunctional acrylates; trifunctional methacrylates; tetrafunctional acrylates; tetrafunctional methacrylates; benzyl acrylate; benzyl methacrylate; phenyl acrylate; phenyl methacrylate, phenoxyalkyl acrylates, phenoxyalkyl methacrylates, phenylalkyl acrylates; phenylalkyl methacrylates; carbazole acrylates; carbazole methacrylates; biphenyl acrylates; biphenyl methacrylates; naphthyl acrylates; naphthyl methacrylates; hydroxyalkyl acrylates and hydroxyalkyl methacrylates, such as 2-hydroxyethyl acrylate, 2-hydroxyethyl methacrylate, 3-hydroxypropyl acrylate, 3-hydroxypropyl methacrylate, 4-hydroxybutyl acrylate, 4-hydroxybutyl methacrylate, 2,3-dihydroxypropyl acrylate, 2,3-dihydroxypropyl methacrylate and the like; acrylamide; N-alkyl acrylamides such as N-methyl acrylamide, N-ethyl acrylamide, N-propyl acrylamide, N-butyl acrylamide and the like; acrylic acid; methacrylic acid; hydroxyethylmethacrylate; 2-phenylpropyl acrylate, 2-phenylpropyl methacrylate, N-hexyl acrylate, ethylene glycol dimethacrylate; ethyl methacrylate; N,N-dimethylacrylamide and combinations of one or more of any of the foregoing. One or more additional dye compound monomers are also included in the reaction in some embodiments. By "combinations" it is meant that combinations of two, three, four, or any other number of monomers are within the scope of the present invention. In some embodiments, the compounds are combined with a prepolymer formed from one or more monomers and combined in a chain extension reaction. In some embodiments, the dye compound is formed into a prepolymer, either alone or with one or more other monomers, then chain extended. In some embodiments, all monomers are combined together for a single reaction. All combinations of reactants and polymerization and chain extension steps are within the present invention.

In some embodiments, other monomers include: methyl methacrylate, 2-hydroxyethyl acrylate, 2-hydroxyethyl methacrylate, 3-hydroxypropyl acrylate, 3-hydroxypropyl methacrylate, n-vinyl pyrrolidone, styrene, eugenol (4-hydroxyvinyl benzene), .alpha.-methyl styrene. In addition, for high-refractive index foldable lens applications, suitable monomers include, but am not limited to: 2-ethylphenoxy methacrylate, 2-ethylphenoxy acrylate, 2-ethylthiophenyl methacrylate, 2-ethylthiophenyl acrylate, 2-ethylaminophenyl methacrylate, phenyl methacrylate, benzyl methacrylate, 2-phenylethyl methacrylate, 3-phenylpropyl methacrylate, 4-phenylbutyl methacrylate, 4-methylphenyl methacrylate, 4-methylbenzyl methacrylate, 2-2-methylphenylethyl methacrylate, 2-3-methylphenylethyl methacrylate, 2-4-methylphenylethyl methacrylate, 2-(4-propylphenyl)ethyl methacrylate; 2-(4-(1-methylethyl)phenyl ethyl methacrylate, 2-(4-methoxyphenyl)ethyl methacrylate, 2-(4-cyclohexylphenyl)ethyl methacrylate, 2-(2-chlorophenyl)ethyl methacrylate, 2-(3-chlorophenyl)ethyl methacrylate, 2-(4-chlorophenyl)ethyl methacrylate, 2-(4-bromophenyl)ethyl methacrylate, 2-(3-phenylphenyl)ethyl methacrylate, 2-(4-phenylphenyl)ethyl methacrylate), 2-(4-benzylphenyl)ethyl methacrylate, and the like, including the corresponding methacrylates, acrylates or combinations thereof. In some embodiments, N-vinyl pyrrolidone, styrene, eugenol and G-methyl styrene are also used for high-refractive index foldable lens applications. In some embodiments, the monomers are a combination of 2-phenylethyl methacrylate (PEMA) and 2-phenylethyl acrylate (PEA).

In some embodiments, the polymerizable composition includes copolymerizable cross-linking agent, such as a terminally ethylenically unsaturated compound having more than one ethylenically-unsaturated polymerizable group. Suitable cross-linking agents include but are not limited to: ethylene glycol dimethacrylate, diethylene glycol dimethacrylate, allyl methacrylate, 1,3-propanediol dimethacrylate, allyl methacrylate, 1,6-hexanediol dimethacrylate, 1,4-butanediol dimethacrylate, and 1,4-butanediol diacrylate (BDDA). Suitable crosslinkers also include polymeric crosslinkers, such as, for example, Polyethylene glycol 1000 Diacrylate, Polyethylene glycol 1000 Dimethacrylate, Polyethylene glycol 600 Dimthacrylate, Polybutanediol 2000 Dimethacrylate, Polypropylene glycol 1000 Diacrylate, Polypropylene glycol 1000 Dimethacrylate, Polytetramethylene glycol 2000 Dimethacrylate, and Polytetramethylene glycol 2000 Diacrylate.

In some embodiments, the polymerizable composition includes one or more thermal free radical initiators. Examples of such initiators include, but are not limited to peroxides, such as benzoyl peroxide, peroxycarbonates, such as bis-(4-tert-butylcyclohexyl)peroxydicarbonate (PERK), azonitriles, such as azo-bis-(isobutyronitrile) (AIBN), and the like.

In some embodiments, the methine chromophores and/or anthraquinone chromophores having ethylenically-unsaturated polymerizable groups may undergo addition reaction to silicone having hydrosilyl groups, the addition reaction using a catalyst such as platinum can provide a silicone compounds having a very little fear of elution of the dye directly bound to the silicone. Examples of the above silicone compounds having hydrosilyl groups are dimethylsiloxane-methylhydrosiloxane copolymer, diphenylsiloxane-phenylhydrosiloxane copolymer, polyethylhydrosiloxane, methylhydrosiloxane-phenylmethylsiloxane copolymer, methylhydrosiloxane-octylmethylsiloxane copolymer, methyl silicone resin containing hydrosilyl groups, polyphenyl(dimethylhydrosiloxy) siloxane and the like, but these are not limited. Catalysts using in the addition reaction of the methine chromophores and/or anthraquinone chromophores having ethylenically-unsaturated polymerizable groups to silicone compounds are desirably platinum compounds such as hydrogen chloroplatinate, platinum-divinyltetramethyldisiloxane, and platinum-tetramethyltetravinylcyclosiloxane. Further, a silicone bound to the methine chromophores and/or anthraquinone chromophores having ethylenically-unsaturated polymerizable groups obtained by the above method provides a silicone elastomer chemically bound to the methine chromophores and/or anthraquinone chromophores by crosslinking with a silicone having vinyl groups. Further, a silicone bound to the above methine chromophores and/or anthraquinone chromophores provides a silicone elastomer chemically bound to the methine chromophores and/or anthraquinone chromophores by crosslinking with a mixture of silicone having vinyl groups and silica. To form the above elastomer, catalysts such as platinum compounds such as hydrogen chloroplatinate, a platinum-divinyltetramethyldisiloxane complex, a platinum-tetramethyltetravinylcyclotetrasiloxane complex and a platinum-alumina supporting catalyst can be used, and such catalysts provide a smooth crosslinking reaction. The methine chromophores and/or anthraquinone chromophores having ethylenically-unsaturated polymerizable groups of the present invention can be chemically bound to silicone having hydrosylil groups and then crosslinked with silicone having vinyl groups. The other method is that the methine chromophores and/or anthraquinone chromophores having ethylenically-unsaturated polymerizable groups of the present invention is mixed with silicone having hydrosilyl groups or silicone having vinyl groups, and the mixture is mixed with silicone having hydrosilyl groups and silicone having vinyl groups, and then the mixture is cross-linked at the same time the methine chromophores and/or anthraquinone chromophores having ethylenically-unsaturated polymerizable groups is reacted to the hydrosilyl groups. At the mixing with silicone described above, it is preferable to homogeneously disperse the methine chromophores and/or anthraquinone chromophores having ethylenically-unsaturated polymerizable groups by using an appropriate solvent. As such solvents, acetone, ethanol, methanol, tetrahydrofuran, dichloromethane can be exemplified. To the solvent, the methine chromophores and/or anthraquinone chromophores having ethylenically-unsaturated polymerizable groups is dissolved and mixed with silicone. Then, the solvent is distilled away with an evaporator, and the methine chromophores and/or anthraquinone chromophores having ethylenically-unsaturated polymerizable groups can be uniformly dispersed in silicone.

The foregoing are simply examples of components that may be in polymerizable compositions and other compositions of the present invention. Every effective combination of two or more of the foregoing components is within the present invention. Furthermore, the foregoing examples are not intended to be limited, and any desirable or acceptable component can be included in the compositions of the present invention.

Polymers and Polymerization Processes

The invention further provides compositions comprising the polymers of the present invention. Such compositions may contain any other suitable component. In some embodiments, the composition includes both one or more polymer(s) of the present invention and one or more light absorbing compound(s) of the present invention. In some embodiments, the compounds are polymerized essentially alone to form polymers formed form monomeric compounds. In some embodiments, the compounds are polymerized along with other monomers.

The polymers contain the residues of free radical polymerization reaction of compounds and other monomers. Any method of free radical polymerization reaction is within the present invention. In addition, the product resulting from polymerization of any of the polymerizable compositions of the present invention, including each combination disclosed above, are also included. Any polymer containing a residue of the free radical polymerization of a compound of the present invention is within the present invention.

The polymerization methods of this invention include all effective polymerization methods including but not limited to free radical, anionic, cationic and living polymerization.

Mixtures are prepared of lens-forming monomers, ultraviolet light absorbing methine compounds and/or violet-blue light blocking (yellow) methine and/or violet-blue light blocking (yellow) anthraquinone monomers in the desired proportions together with a conventional thermal free-radical initiator. The mixture can then be introduced into a mold of suitable shape to form the lens, and the polymerization carded out by gentle heating to activate the initiator. Examples of thermal free radical initiators include, but are not limited to peroxides, such as benzoyl peroxide, peroxycarbonates, such as bis-(4-tert-butylcyclohexyl)peroxydicarbonate (PERK), azonitriles, such as azo-bis-(isobutyronitrile) (AIBN), and the like.

In some embodiments, the monomers are photopolymerized by using a mold which is transparent to actinic radiation of a wavelength capable of initiating polymerization of these acrylic monomers by itself. Conventional photoinitiator compounds, e.g., a benzophenone-type photoinitiator, are optionally introduced to facilitate the polymerization. Photosensitizers can be introduced as well to permit the use of longer wavelengths. In some embodiments of polymers intended for long residence within the eye, the number of ingredients in the polymer is minimized to decrease the risk of having materials leach from the lens into the interior of the eye.

In some embodiments, these monomers are cured directly in a polypropylene mold so that a finished optic is produced. The time and temperature for curing vary with the particular lens-forming material chosen. The optic may be combined in a number of known ways with a variety of known optics to produce an IOL.

Articles

The invention also provides articles that contain the compounds of the present invention, the polymers of the present invention, the compositions of the present invention, or a combination thereof of the present invention. In some embodiments, an entire article is made of one or more compounds, polymers, or compositions of the present invention. In some embodiments, an entire article is made of a mixture, solution, or other combination that includes one or more compound, polymer, or compositions of the present invention. In some embodiments, a component of the article is made is made of one or more compounds, polymers, or compositions of the present invention. In some embodiments, a component of the article is made is made of a mixture, solution, or other combination that includes one or more compound, polymer, or compositions of the present invention. Articles that include more than one compound, polymer, composition, or combination thereof of are also within the present invention.

In some embodiments, the article is or includes a component that is transparent or otherwise permeable to certain wavelengths of visible light. In some embodiments, the article is an optic lens such as lenses useful in windows, contact lenses, telescopes, eyeglasses or sunglasses. In some embodiments, the article is an ocular lens used as an IOL.

In some embodiments, the articles include coatings that contain compounds of the present invention. Such coatings are produced by any means, including but not limited to casting, spin casting, dipping, immersion, or spraying.

In some embodiments, the compounds or polymers are applied in a liquid carrier such as a solvent. After coating, the carrier is removed (for example, by evaporation of the solvent) leaving the compound or polymer on the coated substrate. In some embodiments, the coating is present as a yellow film and/or a UV absorbing film onto a substrate.

Methods of making the articles of the present invention are also within the present invention. In some embodiments, one or more of the polymerizable compounds of this invention are dissolved into a suitable monomer formula, cast onto a substrate (e.g. a transparent material) and cured by a suitable free-radical initiation procedure, such as exposure to heat or UV radiation.

In some embodiments, the compounds of this invention are dissolved into a suitable solvent or monomer formula, followed by immersion of an article or material into the solution containing the compound. The solution enters the polymer (for example, by absorption) then the polymer is dried. The result is incorporation into the matrix of the polymer. The polymerizable compounds are then cured, for example by heat, radiation or other means suitable to bond the compound into the polymer.

This invention can be further illustrated by the following examples, although it will be understood that these examples are included merely for purposes of illustration and are not intended to limit the scope of the invention.

EXAMPLES

Examples 1 through 103 are prophetic examples of some of the compounds that are within the present invention. These examples use Formulas II through VI to describe compound by identifying the various groups in Formulas II through VI. Examples 1 through 94 each identify one compound, Examples 1 through 52 identify compounds using Formula II. Examples 53 through 78 identify compounds using Formula III. For Examples 1 through 78, in cases where numbers are provided along with the identity of the $R_2$ groups in the tables, those numbers indicate the position on the ring in the diagram of Formula II or Formula IV, as applicable. Examples 79 through 94 identify compounds using Formula III. Examples 95 through 103 each identify two compounds because each identify groups (L and Q) that appear (in different locations) on the molecule described in both Formula V and Formula VI. These examples follow, with the formulas provided for reference, each at the beginning of group of Examples to which they apply.

| Example Number | R | R₁ | R₂ | X₁ | X₂ |
|---|---|---|---|---|---|
| 1 | —CH₂CH₃ | —CH₂CH₃ | —H | —CN | —CONH—CH₂CH(CH₃)—OCOC(CH₃)=CH₂ |
| 2 | —CH₃ | —CH₃ | —H | —CN | —CONH—CH₂CH(CH₃)—OCOC(CH₃)=CH₂ |
| 3 | —CH₂CH₂—CN | —CH₂CH₂—CN | 2-CH₃ | —CN | —CONH—CH₂CH(CH₃)—OCOC(CH₃)=CH₂ |
| 4 | —CH₂C₆H₅ | —CH₂C₆H₅ | —H | —CN | —CONH—CH₂CH(CH₃)—OCOC(CH₃)=CH₂ |
| 5 | —CH₂CH₂—CN | —CH₂CH₂—C₆H₅ | —H | —CN | —CONH—CH₂CH(CH₃)—OCOC(CH₃)=CH₂ |
| 6 | 4-ethylphenyl-CO₂CH₃ | 4-ethylphenyl-CO₂CH₃ | —H | —CN | —CONH—CH₂CH(CH₃)—OCOC(CH₃)=CH₂ |
| 7 | —CH₂C₆H₅ | —CH₂C₆H₅ | —H | 2-methylbenzoxazol-yl | —CH₂CH(CH₃)—OCOC(CH₃)=CH₂ |
| 8 | —CH₂CH₃ | —CH₂CH₃ | —H | 2-methylbenzoxazol-yl | 3-isopropenylphenyl-C(CH₃)₂—NHC(O)O—CH(CH₃)CH₂—NHC(O)CH₃ |
| 9 | —CH₃ | —CH₃ | —H | —CN | 3-isopropenylphenyl-C(CH₃)₂—NHC(O)O—CH(CH₃)CH₂—NHC(O)CH₃ |
| 10 | —CH₃ | —CH₂CH₂—CN | —H | —CN | 3-isopropenylphenyl-C(CH₃)₂—NHC(O)O—CH(CH₃)CH₂—NHC(O)CH₃ |

-continued

| Example Number | R | R₁ | R₂ | X₁ | X₂ |
|---|---|---|---|---|---|
| 11 | —CH₃ | —CH₂C₆H₅ | —H | —CN | (3-isopropenylphenyl carbamate group with acetamido propyl linker) |
| 12 | —CH₂CH₂—CN | —CH₂CH₂—OC(O)CH₃ | —H | —CN | (3-isopropenylphenyl carbamate group with acetamido propyl linker) |
| 13 | —(CH₂CH₂O)₃₋₁₀C(O)C(CH₃)=CH₂ | —(CH₂CH₂O)₃₋₁₀C(O)C(CH₃)=CH₂ | —H | —CO₂CH₃ | —CO₂CH₃ |
| 14 | —CH₃ | —(CH₂CH₂O)₃₋₁₀—C(O)C(CH₃)=CH₂ | —H | (2-methylbenzoxazolyl) | —CONH₂ |
| 15 | —(CH₂CH₂O)—C(O)C(CH₃)=CH₂ | —(CH₂CH₂O)—C(O)C(CH₃)=CH₂ | —H | —CO₂CH₃ | —CONH₂ |
| 16 | —(CH₂CH(CH₃)O)—C(O)C(CH₃)=CH₂ | —(CH₂CH(CH₃)O)—C(O)C(CH₃)=CH₂ | —H | —CONH₂ | —CONH₂ |
| 17 | —CH₃ | —COC(CH₃)=CH₂ | H | —CO₂CH₃ | —CO₂CH₃ |
| 18 | —CH₃ | (3-isopropenylphenyl acetamido isopropyl group) | H | —CO₂CH₃ | —CO₂CH₃ |
| 19 | —CH₃ | —COC(CH₃)=CH₂ | —H | —CN | —CN |

-continued

| Example Number | R | R₁ | R₂ | X₁ | X₂ |
|---|---|---|---|---|---|
| 20 | R & R₁ are combined | thianyl dioxide | —H | —CN | cyclohexylmethyl methacrylate with acetamide linker |
| 21 | R & R₁ are combined | thianyl dioxide | —H | —CN | isopropenylphenyl dimethyl carbamate |
| 22 | R & R₁ are combined | thianyl dioxide | —H | —CN | —CONH—CH₂CH(CH₃)—OCOC(CH₃)=CH₂ |
| 23 | R & R₁ are combined | thianyl dioxide | —H | —CONH—CH₂CH(CH₃)—OCOC(CH₃)=CH₂ | —CONH—CH₂CH(CH₃)—OCOC(CH₃)=CH₂ |
| 24 | R & R₁ are combined | thianyl dioxide | —H | isopropenylphenyl dimethyl carbamate with acetamide | isopropenylphenyl dimethyl carbamate with acetamide |
| 25 | R & R₁ are combined | thianyl dioxide | —H | p-tolyl CO₂CH₃ | —CONH—CH₂CH(CH₃)—OCOC(CH₃)=CH₂ |

-continued

| Example Number | R | $R_1$ | $R_2$ | $X_1$ | $X_2$ |
|---|---|---|---|---|---|
| 26 | R & $R_1$ are combined | (thiane-1,1-dioxide ring) | —H | —$C_6H_5$ | —CONH—$CH_2CH(CH_3)$—OCOC($CH_3$)=$CH_2$ |
| 27 | R & $R_1$ are combined | (1,2-diacetylbenzene) | —H | —CONH—$CH_2CH(CH_3)$—OCOC($CH_3$)=$CH_2$ | —CONH—$CH_2CH(CH_3)$—OCOC($CH_3$)=$CH_2$ |
| 28 | R & $R_1$ are combined | (1,2-diacetylbenzene) | —H | (isopropenylphenyl-C(CH$_3$)$_2$-NH-C(O)O-CH(CH$_3$)-CH$_2$-NHC(O)-) | (isopropenylphenyl-C(CH$_3$)$_2$-NH-C(O)O-CH(CH$_3$)-CH$_2$-NHC(O)-) |
| 29 | —($CH_2CH_2O$)—C(O)C($CH_3$)=$CH_2$ | —($CH_2CH_2O$)—C(O)C($CH_3$)=$CH_2$ | —H | (2-ethylhexyl acetate) | (N-methyl acetamide) |
| 30 | —($CH_2CH(CH_3)O$)—C(O)C($CH_3$)=$CH_2$ | —($CH_2CH(CH_3)O$)—C(O)C($CH_3$)=$CH_2$ | —H | (2-ethylhexyl acetate) | (N-(2-ethylhexyl) acetamide) |

-continued

| Example Number | R | R₁ | R₂ | X₁ | X₂ |
|---|---|---|---|---|---|
| 31 | —CH₃ | —COC(CH₃)=CH₂ | —H | —OC(O)CH₂CH(C₂H₅)CH₂CH₂CH₂CH₃ | —OC(O)CH₂CH(C₂H₅)CH₂CH₂CH₂CH₃ |
| 32 | —CH₃ | 1-(3-isopropenylphenyl)-1-methylethyl acetamide group | —H | —OC(O)CH₂CH(C₂H₅)CH₂CH₂CH₂CH₃ | —OC(O)CH₂CH(C₂H₅)CH₂CH₂CH₂CH₃ |
| 33 | —CH₃ | —(CH₂CH₂O)—C(O)C(CH₃)=CH₂ | —H | —C₆H₅ | —CN |
| 34 | —CH₃ | —(CH₂CH(CH₃)O)—C(O)C(CH₃)=CH₂ | —H | —C₆H₅ | —CN |
| 35 | —CH₃ | 4-ethylbenzamido-propyl methacrylate group | —H | —C₆H₅ | —CN |
| 36 | —CH₃ | 4-ethylbenzamido-propyl methacrylate group | —H | —CN | —CN |
| 37 | —CH₃ | 4-ethylbenzamido-propyl methacrylate group | —H | —CO₂CH₃ | —CO₂CH₃ |

-continued

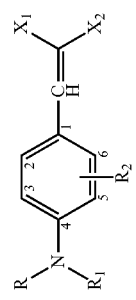

| Example Number | R | $R_1$ | $R_2$ | $X_1$ | $X_2$ |
|---|---|---|---|---|---|
| 38 | —CH$_2$CH$_3$ | —C$_6$H$_{11}$ | 2-Cl | [3-isopropenylphenyl-C(CH$_3$)$_2$-NH-C(=O)-O-CH$_2$CH(CH$_3$)-NH-C(=O)-CH$_3$] | [3-isopropenylphenyl-C(CH$_3$)$_2$-NH-C(=O)-O-CH$_2$CH(CH$_3$)-NH-C(=O)-CH$_3$] |
| 39 | —CH$_2$CH$_3$ | —C$_6$H$_{11}$ | 2-Cl | —CONH—CH$_2$CH(CH$_3$)—OCOC(CH$_3$)=CH$_2$ | —CONH—CH$_2$CH(CH$_3$)—OCOC(CH$_3$)=CH$_2$ |
| 40 | —CH$_2$CH$_2$Cl | —C$_2$H$_5$ | 2-CH$_3$ | [3-isopropenylphenyl-C(CH$_3$)$_2$-NH-C(=O)-O-CH$_2$CH(CH$_3$)-NH-C(=O)-CH$_3$] | [3-isopropenylphenyl-C(CH$_3$)$_2$-NH-C(=O)-O-CH$_2$CH(CH$_3$)-NH-C(=O)-CH$_3$] |
| 41 | —CH$_2$CH$_2$CN | —C$_2$H$_5$ | 2-CH$_3$ | —CONH—CH$_2$CH(CH$_3$)—OCOC(CH$_3$)=CH$_2$ | —CONH—CH$_2$CH(CH$_3$)—OCOC(CH$_3$)=CH$_2$ |
| 42 | R & R$_1$ are combined | thiane-1,1-dioxide | —H | —CN | —CONH—CH$_2$CH(CH$_3$)—OCOCH=CH$_2$ |
| 43 | R & R$_1$ are combined | thiane-1,1-dioxide | —H | —CN | —CONH—CH$_2$CH$_2$—OCOCH=CH$_2$ |
| 44 | —CH$_3$ | —COCH=CH$_2$ | —H | 2-ethylhexyl acetate | 2-ethylhexyl acetate |

-continued

| Example Number | R | R₁ | R₂ | X₁ | X₂ |
|---|---|---|---|---|---|
| 45 | R & R₁ are combined | (tetrahydrothiopyran 1,1-dioxide) | —H | —CN | —CONH—CH₂C(CH₃)₂CH₂OCOC(CH₃)=CH₂ |
| 46 | —CH₂CH₂CN | —CH₂CH₂Cl | —H | —CN | —CONH—CH₂CH(CH₃)—OCOC(CH₃)=CH₂ |
| 47 | —CH₂CH₂CN | (phenylcarbamate propyl ester) | —H | —CN | —CONH—CH₂CH(CH₃)—OCOC(CH₃)=CH₂ |
| 48 | —CH₂CH₂CN | (4-ethyl-methyl benzoate) | —H | —CN | —CONH—CH₂CH(CH₃)—OCOC(CH₃)=CH₂ |
| 49 | —CH₂CH₂CN | (N-propyl succinimide) | —H | —CN | —CONH—CH₂CH(CH₃)—OCOC(CH₃)=CH₂ |

-continued

| Example Number | R | R₁ | R₂ | X₁ | X₂ |
|---|---|---|---|---|---|
| 50 | —CH₂CH₂CN | benzyl | —H | —CN | —CONH—CH₂CH(CH₃)—OCOC(CH₃)=CH₂ |
| 51 | —CH₂CH₂CN | N-propyl phthalimide | —H | —CN | —CONH—CH₂CH(CH₃)—OCOC(CH₃)=CH₂ |
| 52 | —CH₂CH₂CN | propyl phenylcarbamate | —H | —CN | (see structure) |

| Example Number | $R_2$ | $R_3$ | $X_1$ | $X_2$ |
|---|---|---|---|---|
| 53 | —H | —H | —CN | —CONH—CH$_2$CH(CH$_3$)—OCOC(CH$_3$)=CH$_2$ |
| 54 | —H | —CH$_3$ | —CN | —CONH—CH$_2$CH(CH$_3$)—OCOC(CH$_3$)=CH$_2$ |
| 55 | 3-OCH$_3$ | —COC(CH$_3$)=CH$_2$ | —CN | —NH—CH$_2$CH(CH$_3$)—OCOC(CH$_3$)=CH$_2$ |
| 56 | 3-OCH$_3$ | —COC(CH$_3$)=CH$_2$ | —CN | —CO$_2$C$_2$H$_5$ |
| 57 | 3-OCH$_3$ | —(CH$_2$CH$_2$O)—C(O)C(CH$_3$)=CH$_2$ | —CN | —CN |
| 58 | 3-OCH$_3$ | —CH$_2$CH(CH$_3$)O—C(O)C(CH$_3$)=CH$_2$ | —CN | —C$_6$H$_5$ |
| 59 | 3-OCH$_3$ | —CH$_2$CH(CH$_3$)O—C(O)C(CH$_3$)=CH$_2$ | —CN | 2-ethylhexyl acetate group |
| 60 | 3-OCH$_3$ | —CH$_2$CH(CH$_3$)O—C(O)C(CH$_3$)=CH$_2$ | —CN | p-methylbenzamido-propyl methacrylate group |
| 61 | 3-OCH$_3$ | —CH$_2$CH(CH$_3$)O—C(O)C(CH$_3$)=CH$_2$ | —CN | p-methylbenzamido-propyl methacrylate group |
| 62 | —H | —COC(CH$_3$)=CH$_2$ | —CN | —CO$_2$C$_4$H$_{9\text{-}n}$ |
| 63 | —H | —CH$_2$CH(CH$_3$)O—C(O)C(CH$_3$)=CH$_2$ | —CN | —CN |
| 64 | —H | —CH$_2$CH(CH$_3$)O—C(O)C(CH$_3$)=CH$_2$ | —CN | —C$_6$H$_5$ |

-continued

| Example Number | $R_2$ | $R_3$ | $X_1$ | $X_2$ |
|---|---|---|---|---|
| 65 | —H | —(CH$_2$CH(CH$_3$)O)—C(O)C(CH$_3$)=CH$_2$ | —CN | 2-ethylhexyl acetate group |
| 66 | —H | —(CH$_2$CH(CH$_3$)O)—C(O)C(CH$_3$)=CH$_2$ | —CO$_2$C$_2$H$_5$ | —CO$_2$C$_2$H$_5$ |
| 67 | —H | —CH$_3$ | —CN | —CONH(CH$_2$CH$_2$O)$_{6-10}$—(CH$_2$CH(CH$_3$)O)$_{6-10}$COC(CH$_3$)=CH$_2$ |
| 68 | —H | —(CH$_3$CH$_2$O)$_{3-20}$—C(O)C(CH$_3$)=CH$_2$ | —CN | —CO$_2$CH$_3$ |
| 69 | —3-OCH$_3$ | —CH$_3$ | —CN | —NH—CH$_2$CH(CH$_3$)—OCOC(CH$_3$)=CH$_2$ |
| 70 | —3-OCH$_3$ | —CH$_3$ | —CN | —NH—CH$_2$CH$_2$—OCOC(CH$_3$)=CH$_2$ |
| 71 | —3-OCH$_3$ | —CH$_3$ | | methacrylate-O-CH$_2$-cyclohexyl-CH$_2$-NHC(O)CH$_3$ group |
| 72 | —3-OCH$_3$ | —CH$_3$ | —CN | 3-isopropenylphenyl-C(CH$_3$)$_2$-NHC(O)O-CH(CH$_3$)CH$_2$-NHC(O)CH$_3$ group |
| 73 | —3-OCH$_3$ | —CH$_3$ | 3-isopropenylphenyl-C(CH$_3$)$_2$-NHC(O)O-CH(CH$_3$)CH$_2$-NHC(O)CH$_3$ group | 3-isopropenylphenyl-C(CH$_3$)$_2$-NHC(O)O-CH(CH$_3$)CH$_2$-NHC(O)CH$_3$ group |

-continued

| Example Number | $R_2$ | $R_3$ | $X_1$ | $X_2$ |
|---|---|---|---|---|
| 74 | —3-Br | —(CH$_2$CH(CH$_3$)O)—C(O)C(CH$_3$)=CH$_2$ | —CN | ![2-ethylhexyl acetate structure] |
| 75 | —3-OCH$_3$ | —COC(CH$_3$)=CH$_2$ | —CONH—CH$_2$CH(CH$_3$)—OCOC(CH$_3$)=CH$_2$ | —CONH—CH$_2$CH(CH$_3$)—OCOC(CH$_3$)=CH$_2$ |
| 76 | —3-OCH$_3$ | —CH$_2$C$_6$H$_5$ | —CONH—CH$_2$CH(CH$_3$)—OCOC(CH$_3$)=CH$_2$ | —CONH—CH$_2$CH(CH$_3$)—OCOC(CH$_3$)=CH$_2$ |
| 77 | —H | —CH$_2$C$_6$H$_5$ | —CN | —CONH—CH$_2$CH$_2$—O—CH$_2$CH$_2$—OCOC(CH$_3$)=CH$_2$ |
| 78 | —3-OCH$_3$ | H | —CN | —CONH—CH$_2$C(CH$_3$)$_2$CH$_2$OCOC(CH$_3$)=CH$_2$ |

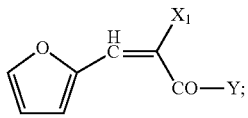

IV

| Example Number | X₁ | Y |
|---|---|---|
| 79 | —CN | —NH—CH₂CH(CH₃)—OCOC(CH₃)=CH₂ |
| 80 | —CN | —NH—CH₂CH(CH₃)—OCOCH=CH₂ |
| 81 | —CN | —NH—CH₂CH₂—OCOC(CH₃)=CH₂ |
| 82 | —CN | ![structure] |
| 83 | —CN | ![structure] |
| 83 | —C(O)CH₃ | —NH—CH₂CH(CH₃)—OCOC(CH₃)=CH₂ |
| 85 | ![phenyl ketone] | —NH—CH₂CH(CH₃)—OCOC(CH₃)=CH₂ |
| 86 | ![p-tolyl CO₂CH₃] | —NH—CH₂CH₂—OCOC(CH₃)=CH₂ |
| 87 | —C(O)CH₃ | ![structure] |
| 88 | ![p-tolyl CO₂CH₃] | ![structure] |
| 89 | —C(O)C(CH₃)₃ | —NH—CH₂C(CH₃)₂CH₂OCOC(CH₃)=CH₂ |
| 90 | ![phenyl ketone] | —NH—CH₂CH(CH₃)—OCOC(CH₃)=CH₂ |
| 91 | —CN | ![structure] |
| 92 | —CN | ![structure] |

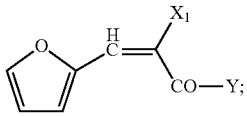

IV

| Example Number | $X_1$ | Y |
|---|---|---|
| 93 | —C(O)C(CH$_3$)$_3$ | 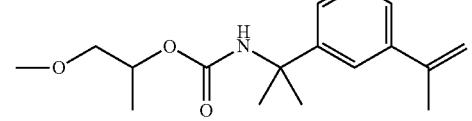 |
| 94 | 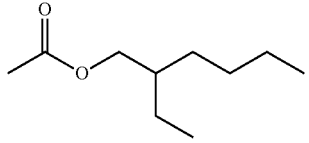 | —O—(CH$_2$CH$_2$O)$_{6-10}$—(CH$_2$CH(CH$_3$)O)$_{6-10}$COC(CH$_3$)=CH$_2$ |

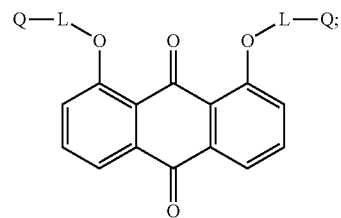

V

| Example | L—Q |
|---|---|
| 95 | —CH$_2$CH(CH$_3$)—OCOC(CH$_3$)=CH$_2$ |
| 96 | —CH$_2$CH$_2$—OCOC(CH$_3$)=CH$_2$ |
| 97 | —CH$_2$CH$_2$—OCOCH=CH$_2$ |
| 98 | 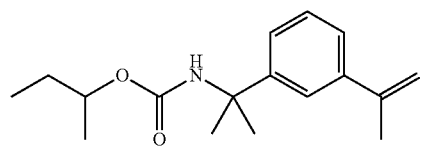 |
| 99 | —(CH$_2$CH$_2$O)$_{6-10}$—(CH$_2$CH(CH$_3$)O)$_{6-10}$COC(CH$_3$)=CH$_2$ |
| 100 | —(CH$_2$)$_{10}$O—COC(CH$_3$)=CH$_2$ |
| 101 | —(CH$_2$CH$_2$O)$_{10-100}$—COC(CH$_3$)=CH$_2$ |
| 102 | —(CH$_2$CH$_2$O)$_{2-5}$—COC(CH$_3$)=CH$_2$ |
| 103 | —(CH$_2$C(CH$_3$)$_2$CH$_2$O)—COCH=CH$_2$ |

Examples 104 through 132 describe actual procedures that were performed in preparing some of the compounds of the present invention and their precursors. Each of Examples 104 through 132 includes a drawing to show the reaction and its product. Stereochemistry of the products of these reactions was not determined, so the diagrams in Examples 104 through 132 should not be interpreted as distinguishing the cis or trans stereoisomer.

Examples 133 through 136 describe examples of some of the procedures for preparing a polymer and polymerizing compounds.

Example 104

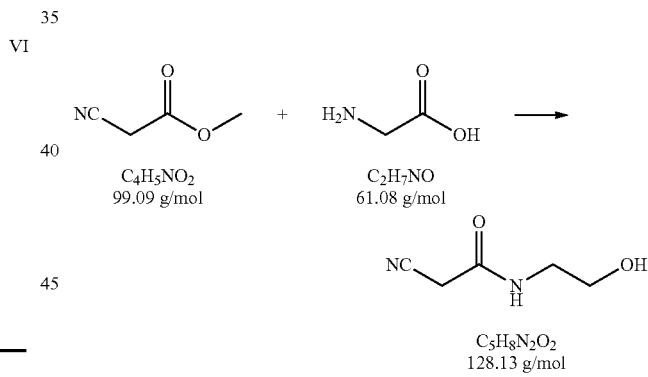

To a clean, dry 1 L 4-neck flask equipped with a mechanical stirrer, heating mantle, thermocouple, addition funnel and a Dean-Stark trap were added 99 g of methyl cyanoacetate (1.0 mol). The reaction vessel was stirred under an atmosphere of dry nitrogen and heated to 95° C. To the reaction vessel were added 61.1 g (1.0 mol) of ethanolamine at a dropwise rate while removing low boilers via the Dean-Stark trap. An exotherm occurred early during the addition and the temperature increased to 105° C. The addition was complete in about 45 minutes and the reaction vessel temperature was increased to 150° C. After about 1 h low boilers were no longer being collected in the Dean-Stark trap. The reaction solution was allowed to cool to about 85° C. and 125 mL of cyclohexane was added at a rapid, dropwise rate. The cyclohexane was decanted. A fresh 75 mL of cyclohexane were added and the warm mixture was transferred to a 600 mL beaker. The product began to solidify to give a waxy solid. The solid was broken upon as much as possible using a spatula and the cyclohexane was decanted. The solid was transferred to a Coors dish and place in the chemical hood to dry overnight. Upon drying the solid had a mass of 120.8 g.

Example 105

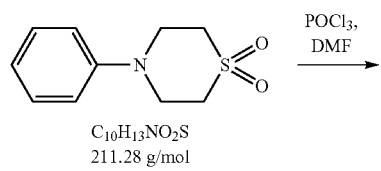

C₁₀H₁₃NO₂S
211.28 g/mol

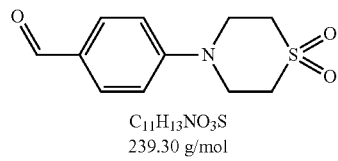

C₁₁H₁₃NO₃S
239.30 g/mol

To a clean, dry 500 mL flask equipped with a heating mantle and addition funnel were added 200 mL of DMF and 50.7 g of N-phenylthiomorpholine-S,S-dioxide (0.2 mol, available from Eastman Chemical Company). The reaction vessel was purged with nitrogen and 20.5 mL of phosphorus oxychloride (0.2 mol) were added at such a rate to keep the temperature from exceeding 35° C. The reaction vessel was heated to 80-90° C. and stirred for about 4 h. The reaction mixture was allowed to cool to room temperature and poured into a mechanically stirred ice water mixture (1 L) containing 100 mL of concentrated ammonium hydroxide. A white precipitate formed that was collected by suction filtration and washed with water. The cake was allowed to dry on the filter overnight to give 54.4 g of product.

Example 106

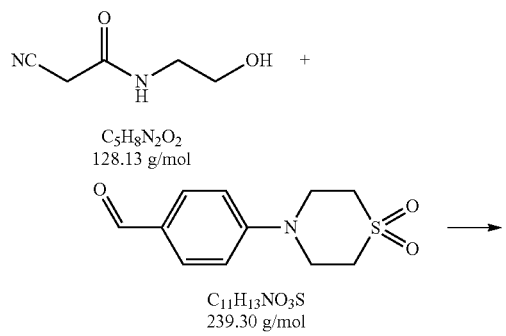

C₅H₈N₂O₂
128.13 g/mol

C₁₁H₁₃NO₃S
239.30 g/mol

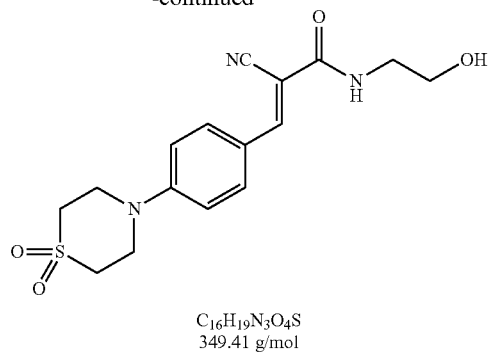

C₁₆H₁₉N₃O₄S
349.41 g/mol

To a 500 mL round-bottomed flask equipped with a mechanical stirrer, reflux condenser and heating mantle were added methanol (175 mL), 18.0 g of product from Example 105 (75.0 mmols) and 10.4 g of product from Example 104 (80.0 mmols). The mixture was heated to reflux and stirred for 3 h then allowed to cool to room temperature, at which time a precipitate formed. The precipitate was collected by suction filtration, washed with cold methanol and allowed to dry on the filter overnight to give 19.75 g of light yellow compound.

Example 107

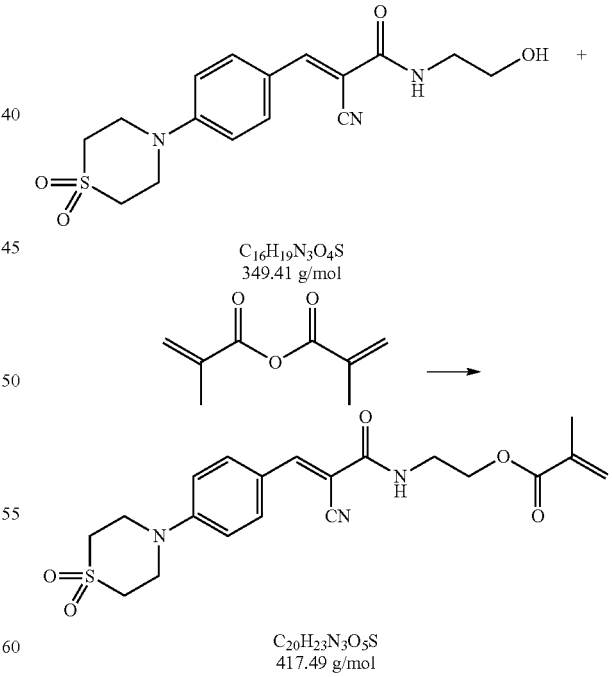

C₁₆H₁₉N₃O₄S
349.41 g/mol

C₂₀H₂₃N₃O₅S
417.49 g/mol

To a clean, dry 50 mL round bottomed flask equipped with a magnetic stirrer and reflux condenser were added 20 mL of acetone, 4.0 g of product from Example 106 (11.4 mmols), 4.3 mL of methacrylic anhydride (28.6 mmols), 4.0 mL of triethylamine (28.6 mmols), 70 mg of 4-dimethylaminopyridine (DMAP, 0.6 mmol) and 40 mg of hydroquinone. The reaction mixture was heated to 50° C. with stirring for about 30 minutes, at which time the starting material was consumed according to TLC analysis (TLC; 1:1 tetrahydrofuran/cyclohexane; $R_f$ (product from Example 106)=0.06; $R_f$ (product from Example 107)=0.32). Upon reaction completion, a precipitate formed. The reaction mixture was allowed to cool to about 30° C. and 20 mL of methanol were added at a dropwise rate. The solid precipitate was collected by suction filtration and washed twice with 20 mL of methanol. The cake was allowed to dry on the filter overnight to give 2.58 g of free flowing yellow powder. The identity of the product was determined to be the target compound by HPLC-MS and the purity was estimated to be about 98%. The compound exhibited a wavelength of maximum absorption ($\lambda_{max}$) at 374.19 nm and a molar absorptivity ($\epsilon$) of 25,900, as determined by Ultraviolet-Visible light spectroscopy (UV-Vis) in N,N-dimethylformamide (DMF) solvent.

Example 108

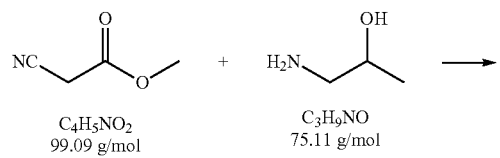

C$_4$H$_5$NO$_2$
99.09 g/mol

C$_3$H$_9$NO
75.11 g/mol

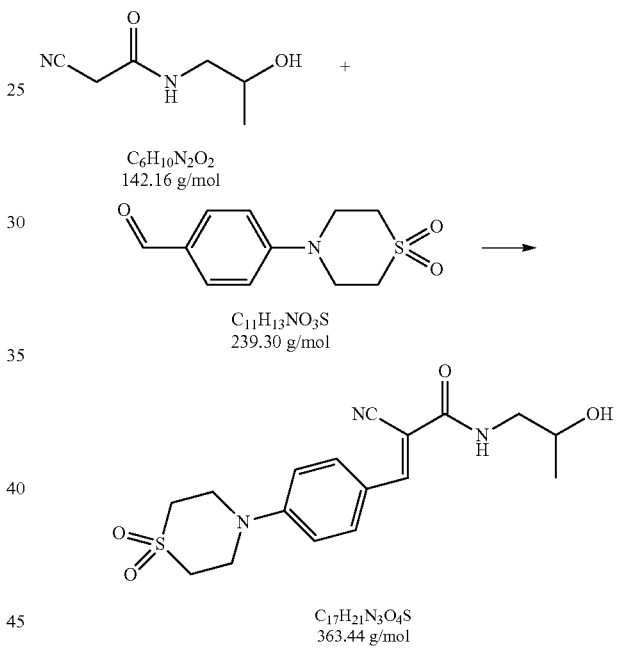

C$_6$H$_{10}$N$_2$O$_2$
142.16 g/mol

To a clean, dry 500 mL 4-neck flask equipped with a mechanical stirrer, heating mantle, thermocouple and a Dean-Stark trap were added 75 g of methyl cyanoacetate (0.75 mol). The reaction vessel was stirred under an atmosphere of dry nitrogen and heated to 95° C. To the reaction vessel were added 58 mL of 1-amino-2-propanol at a dropwise rate while removing low boilers via the Dean-Stark trap. Once the addition was complete, the reaction vessel temperature was increased to 150° C. After about 1 h, low boilers were no longer being collected in the Dean-Stark trap. The reaction solution was allowed to cool to about 50° C. and transferred to a storage vessel to give 103.1 g of an oil that solidified upon standing.

Example 109

C$_6$H$_{10}$N$_2$O$_2$
142.16 g/mol

C$_{11}$H$_{13}$NO$_3$S
239.30 g/mol

C$_{17}$H$_{21}$N$_3$O$_4$S
363.44 g/mol

To a 500 mL round-bottomed flask equipped with a mechanical stirrer, reflux condenser and heating mantle were added methanol (100 mL), 9.0 g of product from Example 105 (37.5 mmols) and 5.7 g of product from Example 108 (40.0 mols). The mixture was heated to reflux and stirred for 3 h then allowed to cool to about 10° C. using an ice-water bath to crystallize the compound. The crystals were collected by suction filtration, washed with cold water and allowed to dry on the filter overnight to give 8.72 g of light yellow compound. The identity of the product was determined to be the target compound by HPLC-MS and the purity was estimated to be about 88%. The compound exhibited a wavelength of maximum absorption ($\lambda_{max}$) at 370.88 nm and a molar absorptivity ($\epsilon$) of 24,600 as determined by Ultraviolet-Visible light spectroscopy (UV-Vis) in DMF solvent.

Example 110

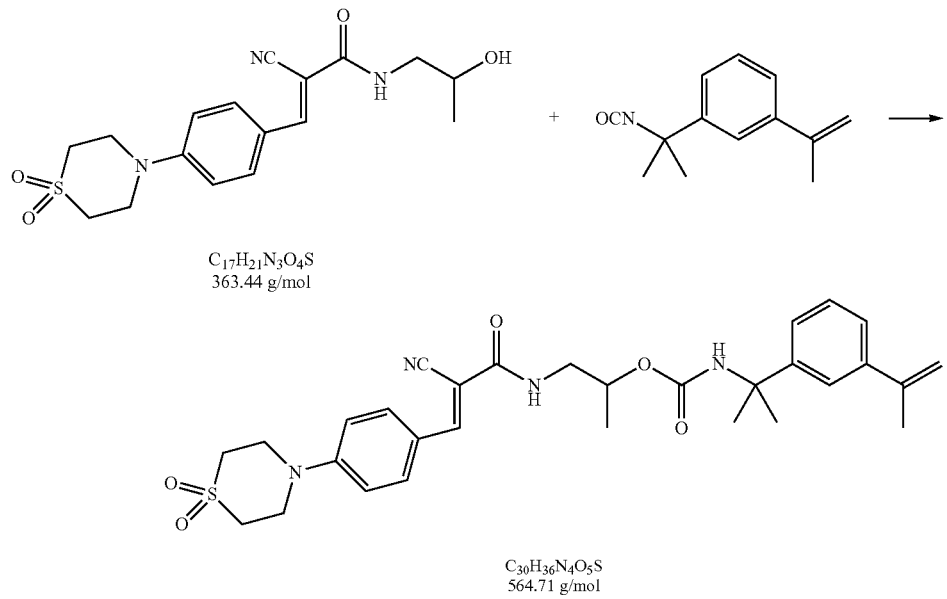

C$_{17}$H$_{21}$N$_3$O$_4$S
363.44 g/mol

C$_{30}$H$_{36}$N$_4$O$_5$S
564.71 g/mol

To a 100 mL round bottomed flask equipped with a magnetic stirrer and heating mantle were added 20 mL of DMF, 1.28 g of 3-isopropenyl-α,α'-dimethylbenzylisocyanate (6 mmols), 2.18 g of product from Example 109 (6 mmols) and 3 drops of dibutyltin dilaurate. The reaction mixture was heated to 90° C. After about 2 h another 10 drops of 3-isopropenyl-α,α'-dimethylbenzylisocyanate were added since TLC analysis revealed that the reaction had not gone to completion. The reaction mixture was allowed to stir for another 2 h at 90° C. then allowed to cool to room temperature. The product compound was precipitated by drowning the reaction mixture, with stirring, into 60 mL of a 50 volume percent solution of methanol and aqueous sodium chloride (10 weight percent). The solid was collected by suction filtration and washed with a 50 volume percent solution of methanol and aqueous sodium chloride (10 weight percent). After drying on the filter overnight, the precipitate had a mass of 0.66 g. The product was determined to be a component of the solid material by HPLC-MS and the purity was estimated to be about 40%. The compound exhibited a wavelength of maximum absorption ($\lambda_{max}$) at 388 nm as determined by Ultraviolet-Visible light spectroscopy (UV-Vis) in DMF solvent.

Example 111

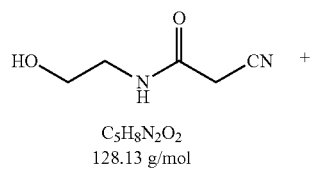

C$_5$H$_8$N$_2$O$_2$
128.13 g/mol

-continued

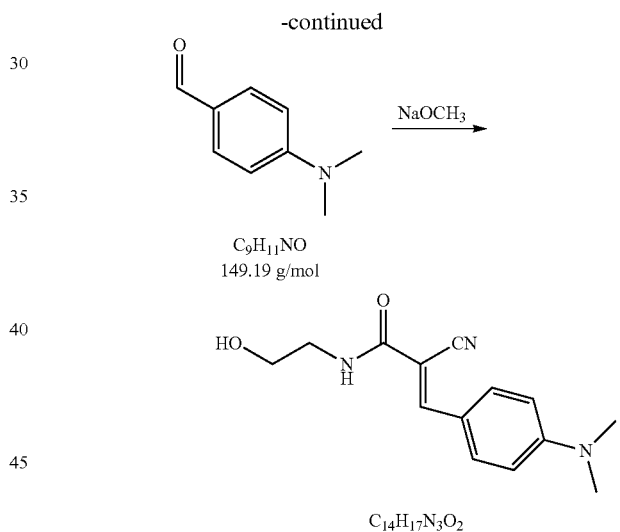

C$_9$H$_{11}$NO
149.19 g/mol

C$_{14}$H$_{17}$N$_3$O$_2$
259.31 g/mol

To a clean, dry 100 mL round bottomed flask equipped with a magnetic stirrer and reflux condenser were added 25 mL of anhydrous ethanol, 4.0 g of product from Example 104 (31.2 mmols), 4.43 g of 4-N,N-dimethylaminobenzaldehyde (29.7 mmols) and 4 drops of a 25 weight percent solution of sodium methoxide in methanol. The reaction mixture was heated to reflux with stirring until the 4-N,N-dimethylaminobenzaldehyde had be consumed according to TLC analysis (TLC; 1:1 tetrahydrofuran/cyclohexane; R$_f$ (product from Example 111)=0.20). Upon reaction completion the reaction solution was allowed to cool to room temperature and stir overnight. A precipitate formed. The precipitate was collected by suction filtration and washed with about 25 mL of methanol. The cake was allowed to dry on the filter overnight to give 2.87 g of free flowing yellow powder. The identity of the product was determine to be the target compound by HPLC-MS and the purity was estimated to be about 96%. The compound exhibited a wavelength of maximum absorption ($\lambda_{max}$) at 422 nm as determined by Ultraviolet-Visible light spectroscopy (UV-Vis) in DMF solvent.

Example 112

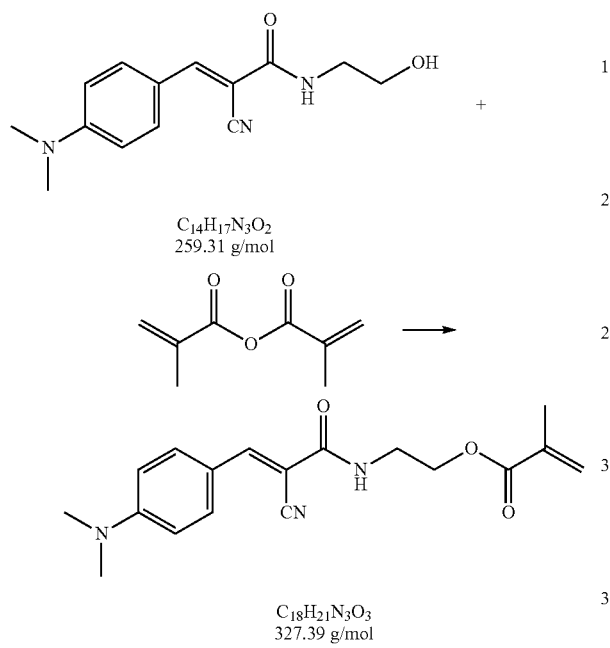

To a clean, dry 50 mL round bottomed flask equipped with a magnetic stirrer and reflux condenser were added 10 mL of acetone, 1.0 g of product from Example 111 (3.86 mmols), 0.72 mL of methacrylic anhydride (4.82 mmols), 0.67 mL of triethylamine (4.82 mmols), 23.6 mg of 4-dimethylaminopyridine (DMAP, 0.19 mmols) and 10 mg of hydroquinone. The reaction mixture was heated to 50° C. with stirring for about 35 minutes, at which time the starting material was consumed according to TLC analysis (TLC; 1:1 tetrahydrofuran/cyclohexane; $R_f$ (product from Example 111)=0.19; $R_f$ (product from Example 112)=0.50). The reaction mixture was allowed to cool to room temperature and product from Example 112 was precipitated by adding 12 mL of a 5:1 solution of water in methanol at a dropwise rate while stirring. The solid precipitate was collected by suction filtration and washed with 6.0 mL of a 5:1 solution of water in methanol. The cake was allowed to dry on the filter overnight to give 1.26 g of free flowing yellow powder. The identity of the product was determined to be the target compound by HPLC-MS and the purity was estimated to be about 93%. The compound exhibited a wavelength of maximum absorption ($\lambda_{max}$) at 392.08 nm and a molar absorptivity ($\epsilon$) of 28,800 as determined by Ultraviolet-Visible light spectroscopy (UV-Vis) in DMF solvent.

Example 113

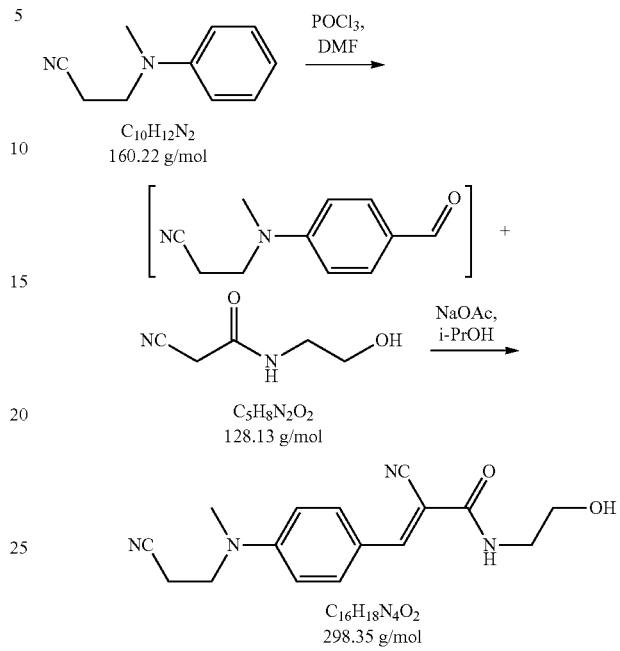

Part I.

To a clean, dry 500 mL flask equipped with a heating mantle and addition funnel were added 50 mL of DMF and 16.0 g of N-methyl-N-2-cyanoethylaniline (0.1 mol). The reaction vessel was purged with nitrogen and 10.0 mL of phosphorus oxychloride (0.2 mols) were added at such a rate to keep the temperature from exceeding 35° C. The temperature was regulated using an ice water bath. The reaction vessel was heated to 80-90° C. and stirring for about 2 h. The reaction mixture was allowed to cool to about 40° C.

Part II.

A portion of the product from Example 104 (12.8 g, 0.1 mol) was dissolved into 200 mL of isopropyl alcohol in a 1 L beaker. Anhydrous sodium acetate (40.0 g) was added to the beaker, the mixture was stirred and the beaker was heated to 75° C. To this mixture was added the reaction mixture from Part I (Vilsmeier complex) at a fairly rapid rate. When the addition was complete, the reaction mixture was stirred for an additional 1 h and allowed to cool to room temperature. The reaction mixture was added at a rapid dropwise rate to 400 mL of an ice water solution. The dark mixture was transferred to a 4 L beaker equipped with a mechanical stirrer and stirred. Water (350 mL) was added at a dropwise rate and the solution became cloudy. Another 400 mL of water were added with stirring and the compound began to precipitate. The precipitate was collected by suction filtration and washed with cold water followed by warm water. The cake was allowed to dry on the filter overnight to give 17.5 g of compound. The identity of the product was determined to be the target compound by HPLC-MS and the purity was estimated to be about 95%. The compound exhibited a wavelength of maximum absorption ($\lambda_{max}$) at 381.8 nm and a molar absorptivity ($\epsilon$) of 27,000 as determined by Ultraviolet-Visible light spectroscopy (UV-Vis) in DMF solvent.

Example 114

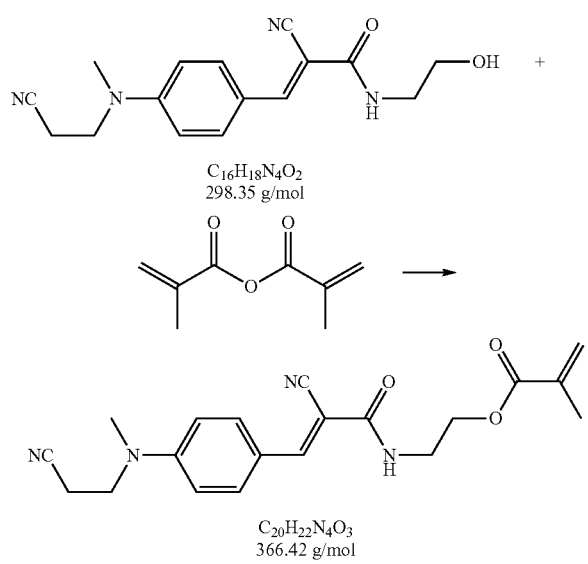

C_{16}H_{18}N_4O_2
298.35 g/mol

C_{20}H_{22}N_4O_3
366.42 g/mol

To a clean, dry 50 mL round bottomed flask equipped with a magnetic stirrer and reflux condenser were added 50 mL of acetone, 3.5 g of product from Example 113 (11.7 mmols), 2.5 mL of methacrylic anhydride (16.8 mmols), 2.0 mL of triethylamine (16.8 mmols), 70 mg of 4-dimethylaminopyridine (DMAP, 0.6 mmlos) and 30 mg of hydroquinone. The reaction mixture was heated to 50-55° C. with stirring for about 45 minutes, at which time the starting material had not been consumed according to TLC analysis (TLC; 1:1 tetrahydrofuran/cyclohexane). Another 10 drops of methacrylic anhydride were added to the reaction mixture. The reaction mixture was stirred for an additional 30 minutes then allowed to cool to room temperature and the product was precipitated by adding about 50 mL of a 5:1 solution of water in methanol at a dropwise rate while stirring. The solid precipitate was collected by suction filtration and washed with water. The cake was allowed to dry on the filter overnight to give 3.43 g of yellow powder. The identity of the product was determined to be the target compound by HPLC-MS and the purity was estimated to be about 92%. The compound exhibited a wavelength of maximum absorption ($\lambda_{max}$) at 381.8 nm and a molar absorptivity ($\epsilon$) of 28,300 as determined by Ultraviolet-Visible light spectroscopy (UV-Vis) in DMF solvent.

Example 115

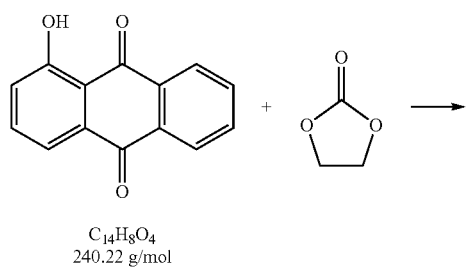

C_{14}H_8O_4
240.22 g/mol

C_{18}H_{16}O_6
328.32 g/mol

To a 500 mL round bottomed flask equipped with a magnetic stirrer, thermocouple and heating mantle were added 24 g of 1,8-dihydroxyanthraquinone (0.1 mole), 88 g of ethylene carbonate (1.0 mole), 0.5 g of tetramethylammonium chloride and 75 mL of ethylene glycol. The reaction mixture was heated to 150° C. for 20 h. TLC analysis revealed that the starting material had been consumed. The reaction mixture was allowed to cool to about 80° C. and the product was precipitated by adding 500 mL of warm water with stirring. The solid was collected by suction filtration, washed with hot water and allowed to dry on the filter overnight to give 21.0 g of a tacky solid. The solid material was broken up and added to a 2 L beaker containing toluene. The mixture was heated to boiling while constantly stirring. The mixture was allowed to cool to about 80° C. and filtered. The solid was collected and washed with toluene and allowed to dry on the filter overnight to give 16.8 g of product. The identity of the product was determined to be the target compound by HPLC-MS and the purity was estimated to be about 85%. An ethylenically-unsaturated polymerizable group can be readily attached to the hydroxyethyl groups on the product by any effective means, for example by reaction with an appropriate anhydride such as methacrylic anhydride as in Example 114.

Example 116

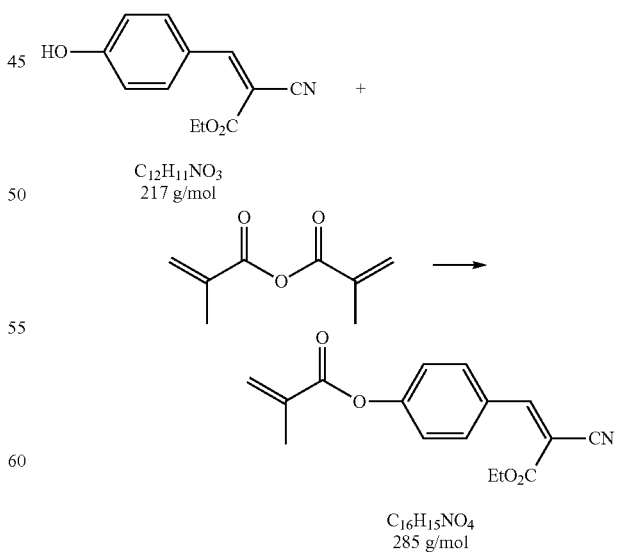

C_{12}H_{11}NO_3
217 g/mol

C_{16}H_{15}NO_4
285 g/mol

To a clean, dry 100 mL round bottomed flask equipped with a magnetic stirrer were added 20 mL of DMF, 10.0 g of ethyl 2-cyano-3-(hydroxyphenyl)propenoate (46.1 mmols, for preparation see U.S. Pat. No. 4,617,374, Example A), 13.7 mL of methacrylic anhydride (92.2 mmols), 12.9 mL of triethylamine (92.2 mmols), 563 mg of 4-dimethylaminopyridine (DMAP, 4.6 mmlos) and 100 mg of hydroquinone. The reaction mixture was stirred at room temperature for about 18 h. The product was precipitated by drowning the reaction mixture into 50 mL of water. The solid precipitate was collected by suction filtration and washed with water. The cake was allowed to dry on the filter overnight to give 10.60 g of off white powder. The identity of the product was determined to be the target compound by HPLC-MS and the purity was estimated to be about 96%. The compound exhibited a wavelength of maximum absorption ($\lambda_{max}$) at 312 nm as determined by Ultraviolet-Visible light spectroscopy (UV-Vis) in DMF solvent.

Example 117

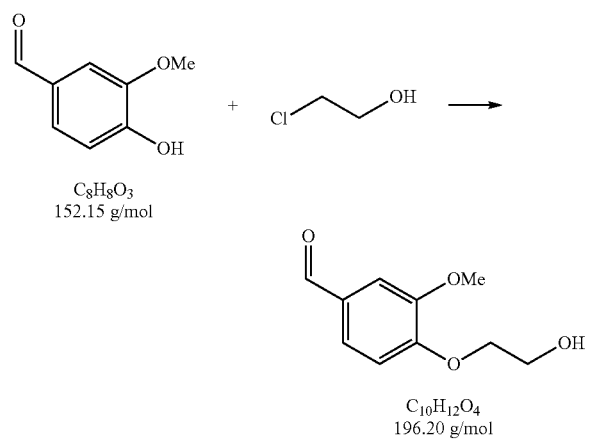

To a 1 L flask equipped with a mechanical stirrer and heating mantle were added 53 g of 50 weight percent aqueous sodium hydroxide (0.66 mol) and 375 mL of warm water with stirring. Vanillin (68.4 g, 0.45 mol) was added followed by the dropwise addition of 53 mL of 2-chloroethanol (0.54 mol) over about 1 h. During the addition of 2-chloroethanol, the reaction mixture was gradually heated to 100° C. The reaction mixture was stirred at 100° C. for an additional 16 h and allowed to cool to room temperature. The reaction mixture was composed of two phases that tested acidic according to pH test strips. The mixture was stirred and made basic by adding about 5 mL of concentrated ammonium hydroxide to give a solution. The solution was poured onto about 400 g of ice that caused the desired product to precipitate. The precipitate was collected by suction filtration, washed with cold water and allowed to dry on the filter overnight to give 70.6 g of product. The solid product had a melting point range of 94-96° C. HPLC-MS analysis was used to confirm the identity of the product and the purity was estimated to be 94%.

Example 118

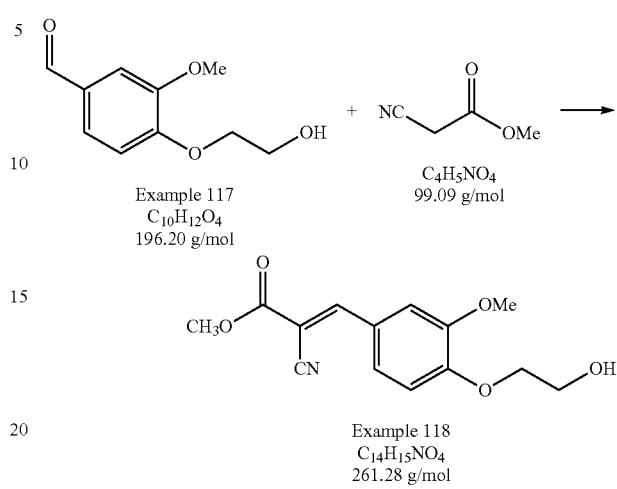

To a clean, dry 500 mL round bottomed flask equipped with a magnetic stirrer and reflux condenser were added 150 mL of methanol, 39.2 g of product from Example 117 (0.2 mols), 19.8 g of methyl cyanoacetate (0.2 mols) and 5 drops of piperidine. The reaction mixture was heated to reflux with stirring for 1.5 h. Upon reaction completion the reaction solution was allowed to cool to room temperature at which time the material began to precipitate. Another 50 mL of chilled methanol were added and the precipitate was collected by suction filtration. The cake was washed with a small amount of chilled methanol and allowed to dry on the filter overnight to give 49.6 g of free flowing yellow powder. The identity of the product was determined to be the target compound by HPLC-MS and the purity was estimated to be about 97%. The compound exhibited a wavelength of maximum absorption ($\lambda_{max}$) at 366.8 nm and a molar absorptivity ($\epsilon$) of 22,400 as determined by Ultraviolet-Visible light spectroscopy (UV-Vis) in DMF solvent.

Example 119

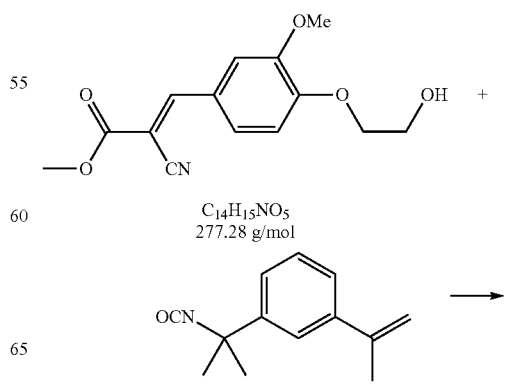

-continued

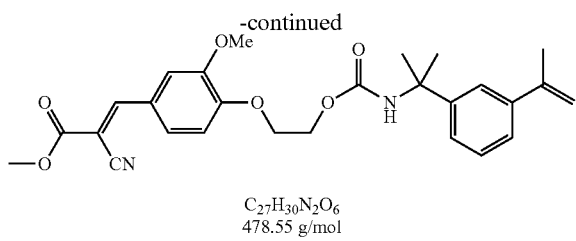

C$_{27}$H$_{30}$N$_2$O$_6$
478.55 g/mol

To a 100 mL round bottomed flask equipped with a magnetic stirrer and heating mantle were added 25 mL of toluene, 0.8 g of 3-isopropenyl-α,α'-dimethylbenzylisocyanate (4.0 mmols), 1.04 g of methyl 2-cyano-3-(4-hydroxyethoxy-3-methoxyphenyl)propenoate (3.75 mmols, Example 118) and 3 drops of dibutyltin dilaurate. The reaction mixture was heated to 90° C. After about 45 minutes, the reaction was complete according to TLC analysis (1:1 THF/Cyclohexane). The reaction mixture was allowed to cool to room temperature. The product was precipitated by drowning the reaction mixture, with stirring, into 200 mL of heptane. The yellow solid was collected by suction filtration and washed with heptane and allowed to dry on the filter overnight to give 1.5 g of product. The identity of the product was determined to be the target compound by HPLC-MS and the purity was estimated to be about 94%. The compound exhibited a wavelength of maximum absorption ($\lambda_{max}$) at 362.0 nm as determined by Ultraviolet-Visible light spectroscopy (UV-Vis) in DMF solvent.

Example 120

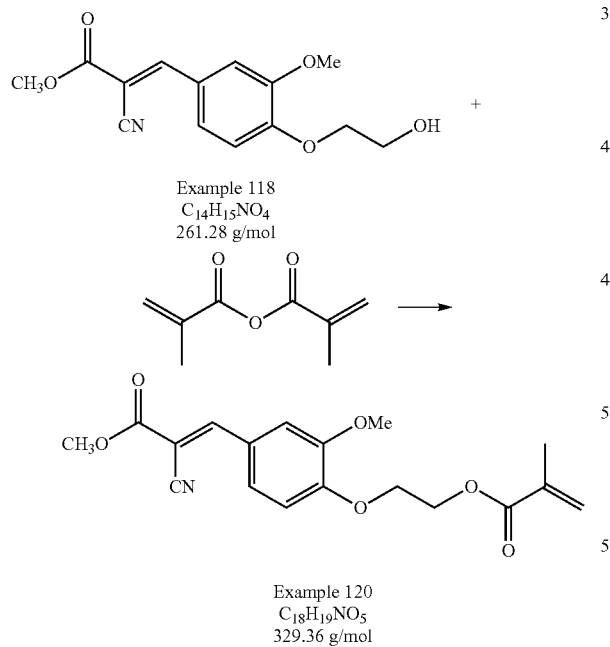

Example 118
C$_{14}$H$_{15}$NO$_4$
261.28 g/mol

Example 120
C$_{18}$H$_{19}$NO$_5$
329.36 g/mol

To a clean, dry 1 L round bottomed flask equipped with a magnetic stirrer and reflux condenser were added 200 mL of acetone, 33.2 g of product from Example 118 (0.12 mol), 23.0 mL of methacrylic anhydride (0.15 mmol), 20.0 mL of triethylamine (0.14 mol), 0.7 g of 4-dimethylaminopyridine (DMAP, 5.7 mmlos) and 400 mg of hydroquinone. The reaction mixture was heated to 50-55° C. with stirring for about 45 minutes, at which time the starting material had not been consumed according to TLC analysis (TLC; 1:1 tetrahydrofuran/cyclohexane). Another 2-3 mL of methacrylic anhydride were added to the reaction mixture. The reaction mixture was stirred for an additional 30 minutes then allowed to cool to room temperature and the product was precipitated by adding about 350 mL of cold water at a rapid rate while stirring. The solid precipitate was collected by suction filtration, washed with water and washed with a small amount of cold methanol. The cake was allowed to dry on the filter overnight to give 37.1 g of yellow powder. The identity of the product was determined to be the target compound by HPLC-MS and the purity was estimated to be about 95%. The compound exhibited a wavelength of maximum absorption ($\lambda_{max}$) at 362.8 nm and a molar absorptivity ($\epsilon$) of 21,800 as determined by Ultraviolet-Visible light spectroscopy (UV-Vis) in DMF solvent.

Example 121

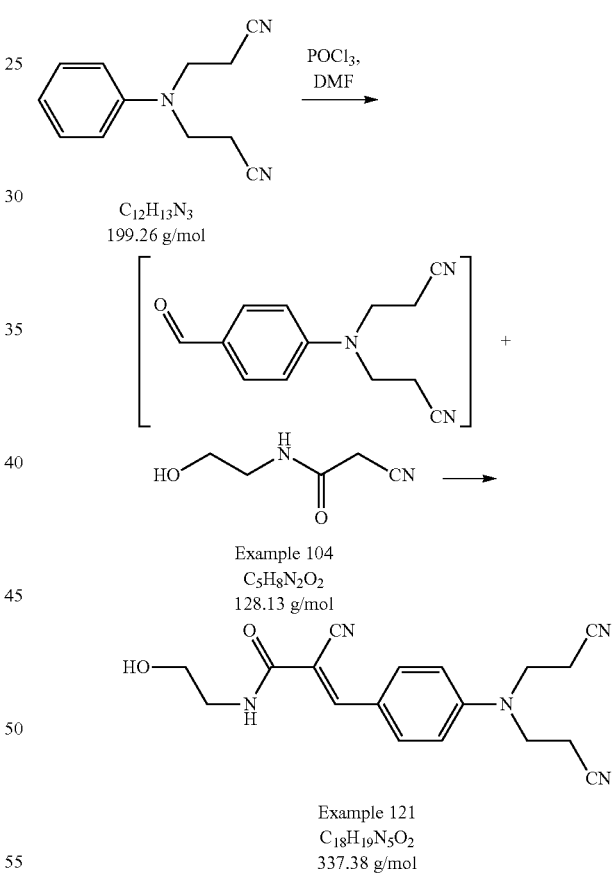

C$_{12}$H$_{13}$N$_3$
199.26 g/mol

Example 104
C$_5$H$_8$N$_2$O$_2$
128.13 g/mol

Example 121
C$_{18}$H$_{19}$N$_5$O$_2$
337.38 g/mol

Part I.

To a clean, dry 300 mL flask equipped with a heating mantle and addition funnel were added 40 mL of DMF and 12.5 g of 3,3'-(phenylimino)dipropionitrile (0.06 mol). The reaction vessel was purged with nitrogen and 6.5 mL of phosphorus oxychloride (0.042 mol) were added at such a rate to keep the temperature from exceeding 35° C. The temperature was regulated using an ice water bath. The reaction vessel was heated to 80-90° C. and stirred for about 1 h. The reaction mixture was allowed to cool to about 40° C.

Part II.

A portion of the product from Example 104 (7.7 g, 0.6 mol) was dissolved into 90 mL of absolute ethanol in a 1 L beaker. Anhydrous sodium carbonate (24 g) was added to the beaker, the mixture was stirred and the beaker was heated to 75° C. To this mixture was added the mixture from Part I (Vilsmeier complex) at a fairly rapid rate. When the addition was complete, the reaction mixture was stirred for an additional 1 h at 75° C. and allowed to cool to room temperature. The reaction mixture was added at a rapid dropwise rate to 400 mL of ice water to precipitate the product. The precipitate was collected by suction filtration and washed with warm water. The cake was allowed to dry on the filter overnight to give 13.9 g of product. The identity of the product was determined to be the target compound by HPLC-MS and the purity was estimated to be about 97%. The compound exhibited a wavelength of maximum absorption ($\lambda_{max}$) at 369.91 nm and a molar absorptivity ($\epsilon$) of 28,400 as determined by Ultraviolet-Visible light spectroscopy (UV-Vis) in DMF solvent.

Example 122

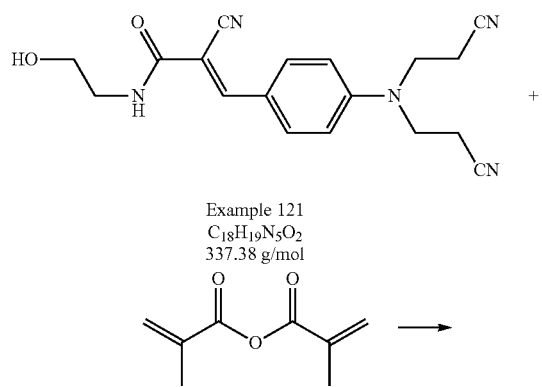

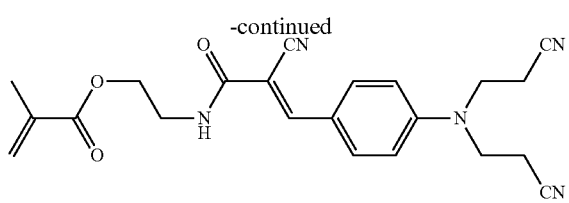

Example 122
$C_{22}H_{23}N_5O_3$
405.45 g/mol

To a clean, dry 100 mL round bottomed flask equipped with a magnetic stirrer and reflux condenser were added 50 mL of acetone, 3.95 g of product from Example 121 (11.7 mmols), 2.5 mL of methacrylic anhydride (16.8 mmols), 2.0 mL of triethylamine (14.3 mmols), 0.07 g of 4-dimethylaminopyridine (DMAP, 0.6 mmlos) and 40 mg of hydroquinone. The reaction mixture was heated to 50° C. with stirring for about 45 minutes, at which time the starting material had been consumed according to TLC analysis (TLC; 75:25 tetrahydrofuran/cyclohexane). The reaction mixture was stirred for an additional 20 minutes then allowed to cool to room temperature and the product was precipitated by adding about 50 mL of cold water at a moderate rate while stirring. The solid precipitate was collected by suction filtration, washed with water and washed with a small amount of a 4:1 solution of water and methanol, respectively. The cake was allowed to dry on the filter overnight to give 3.77 g of light yellow powder. The identity of the product was determined to be the target compound by HPLC-MS and the purity was estimated to be about 94%. The compound exhibited a wavelength of maximum absorption ($\lambda_{max}$) at 370.9 nm and a molar absorptivity ($\epsilon$) of 30,100 as determined by Ultraviolet-Visible light spectroscopy (UV-Vis) in DMF solvent.

Example 123

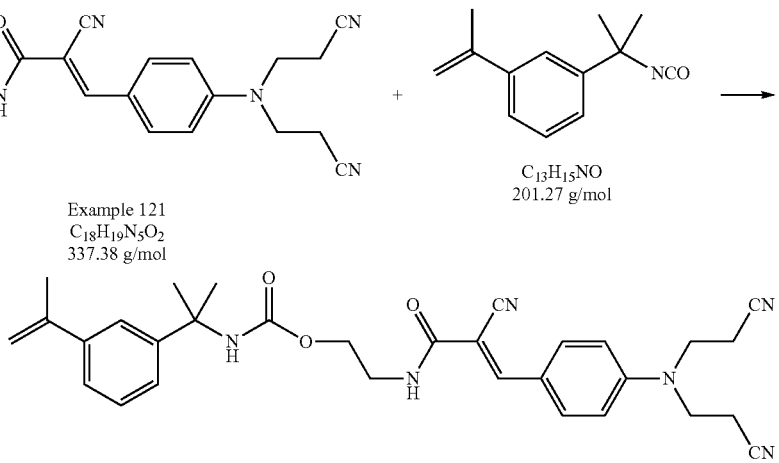

Example 123
$C_{31}H_{34}N_6O_3$
538.66 g/mol

To a 100 mL round bottomed flask equipped with a magnetic stirrer and heating mantle were added 35 mL of toluene, 2.5 g of 3-isopropenyl-α,α'-dimethylbenzylisocyanate (12.4 mmols), 3.4 g of the product from example 121 (10 mmols) and 4 drops of dibutyltin dilaurate. The reaction mixture was heated to 90-95° C. After about 2 h, the reaction was complete according to TLC analysis (72:25 THF/Cyclohexane). The reaction mixture was allowed to cool to about 65° C. and added slowly to a moderately stirred beaker containing 50 mL of heptane to precipitate the product. The resulting slurry was further cooled to 15-20° C. using an ice-water bath. The light yellow solid was collected by suction filtration, washed with heptane and allowed to dry on the filter overnight to give 4.27 g of product. The identity of the product was determined to be the target compound by HPLC-MS and the purity was estimated to be about 79%. The compound exhibited a wavelength of maximum absorption ($\lambda_{max}$) at 371.26 nm and a molar absorptivity ($\epsilon$) of 24,600 as determined by Ultraviolet-Visible light spectroscopy (UV-Vis) in DMF solvent.

Example 124

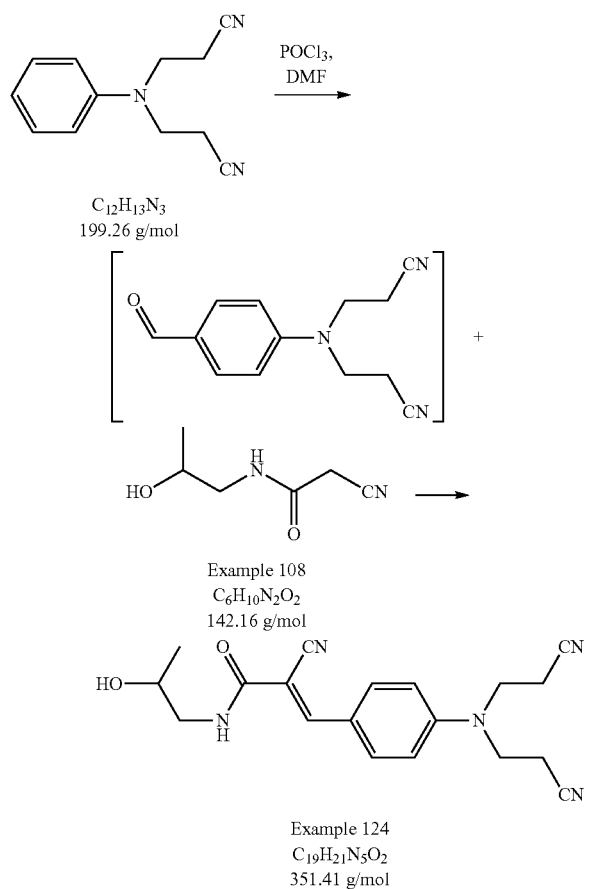

Part I.

To a clean, dry 300 mL flask equipped with a heating mantle and addition funnel were added 40 mL of DMF and 12.5 g of 3,3'-(phenylimino)dipropionitrile (0.06 mol). The reaction vessel was purged with nitrogen and 6.5 mL of phosphorus oxychloride were added at such a rate to keep the temperature from exceeding 35° C. The temperature was regulated using an ice water bath. The reaction vessel was heated to 80-90° C. and stirred for about 2 h. The reaction mixture was allowed to cool to about 40° C.

Part II.

A portion of the product from Example 108 (8.5 g, 0.6 mol) was dissolved into 75 mL of absolute ethanol in a 1 L beaker. Anhydrous sodium acetate (24 g) was added to the beaker, the mixture was stirred and the beaker was heated to 75° C. To this mixture was added the mixture from Part I (Vilsmeier complex) at a fairly rapid dropwise rate. When the addition was complete, the reaction mixture was stirred for an additional 1 h at 75° C. and allowed to cool to room temperature. The reaction mixture was added at a rapid dropwise rate to 400 mL of ice water to precipitate the product. The precipitate was collected by suction filtration and washed with cold water followed by warm water. The cake was allowed to dry on the filter overnight to give 17.5 g of product. The identity of the product was determined to be the target compound by HPLC-MS and the purity was estimated to be about 84%. The compound exhibited a wavelength of maximum absorption ($\lambda_{max}$) at 371.25 nm and a molar absorptivity ($\epsilon$) of 30,700 as determined by Ultraviolet-Visible light spectroscopy (UV-Vis) in DMF solvent.

Example 125

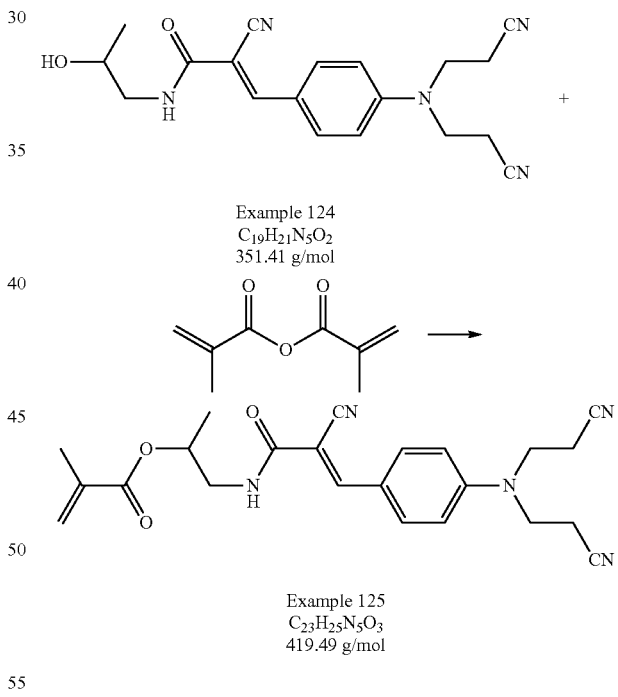

To a clean, dry 100 mL round bottomed flask equipped with a magnetic stirrer and reflux condenser were added 40 mL of acetone, 3.15 g of product from Example 124 (9.0 mmols), 1.8 mL of methacrylic anhydride (12.6 mmols), 1.5 mL of triethylamine (10.8 mmols), 0.05 g of 4-dimethylaminopyridine (DMAP, 0.4 mmol) and 30 mg of hydroquinone. The reaction mixture was heated to 50° C. with stirring for about 1 h. A small amount of Example 124 remained according to TLC analysis (TLC; 75:25 tetrahydrofuran/cyclohexane). An additional 25 drops of methacrylic anhydride were added. The reaction mixture was stirred for an additional 2 h. TLC analysis revealed that a slight amount of Example 124 remained thus another 10 drops of methacrylic anhydride were added. The reaction mixture was stirred for an additional 1 h then allowed to cool to room temperature and stir overnight. The product was precipitated by adding about 50 mL of cold water at a dropwise rate while stirring. The solid precipitate was collected by suction filtration, washed with water and allowed to dry on the filter overnight to give 3.15 g of light yellow powder. The identity of the product was determined to be the target compound by HPLC-MS and the purity was estimated to be about 89%. The compound exhibited a wavelength of maximum absorption ($\lambda_{max}$) at 371.71 nm and a molar absorptivity ($\epsilon$) of 30,500 as determined by Ultraviolet-Visible light spectroscopy (UV-Vis) in DMF solvent.

Example 126

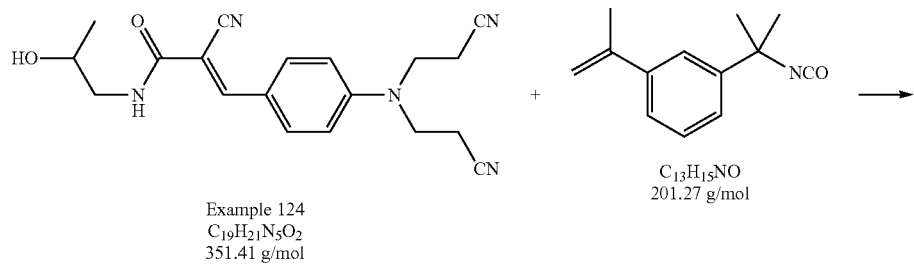

Example 124
$C_{19}H_{21}N_5O_2$
351.41 g/mol $C_{13}H_{15}NO$
201.27 g/mol

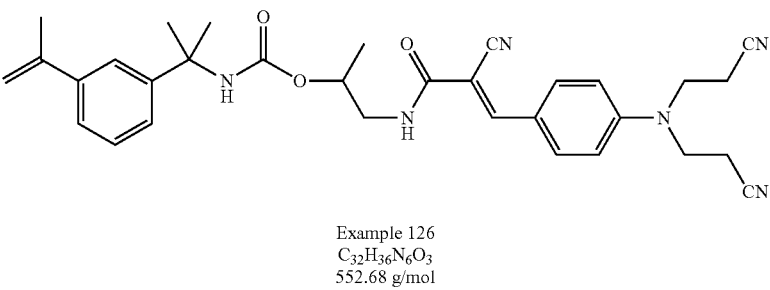

Example 126
$C_{32}H_{36}N_6O_3$
552.68 g/mol

To a 100 mL round bottomed flask equipped with a magnetic stirrer and heating mantle were added 50 mL of toluene, 2.5 g of 3-isopropenyl-α,α'-dimethylbenzylisocyanate (12.4 mmols), 3.15 g of the product from example 124 (9 mmols) and 3 drops of dibutyltin dilaurate. The reaction mixture was heated to 90-95° C. After about 5 h, TLC analysis revealed that some of Example 124 remained (72:25 THF/Cyclohexane). Another 15 drops of 3-isopropenyl-α,α'-dimethylbenzylisocyanate, 10 mL of toluene and 3 drops of dibutyltin dilaurate were added. The reaction mixture was stirred at 90-95° C. for an additional 4 h. The reaction mixture was allowed to about 40° C. and added slowly to a moderately stirred beaker containing 125 mL of heptane to precipitate the product. The light yellow solid was collected by suction filtration, washed with heptane and allowed to dry on the filter overnight to give 5.49 g of product. The identity of the product was determined to be the target compound by HPLC-MS and the purity was estimated to be about 73%. The compound exhibited a wavelength of maximum absorption ($\lambda_{max}$) at 372.72 nm and a molar absorptivity ($\epsilon$) of 23,900 as determined by Ultraviolet-Visible light spectroscopy (UV-Vis) in DMF solvent.

Example 127

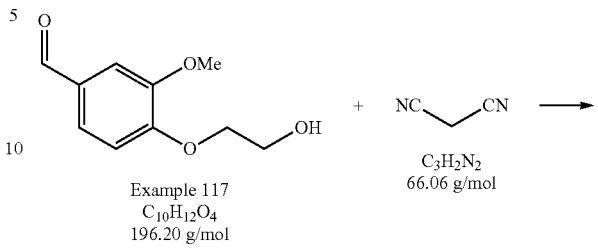

Example 117
$C_{10}H_{12}O_4$
196.20 g/mol $C_3H_2N_2$
66.06 g/mol

-continued

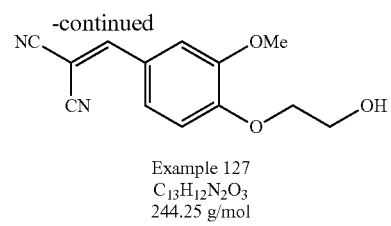

Example 127
$C_{13}H_{12}N_2O_3$
244.25 g/mol

To a clean, dry 100 mL round bottomed flask equipped with a magnetic stirrer and reflux condenser were added 40 mL of methanol, 5.88 g of product from Example 117 (30.0 mmols), 2.0 g of malononitrile (30.0 mmols) and 5 drops of piperidine. The reaction mixture was heated to reflux with stirring for 1.5 h. Solid product began to form by the time the reaction had reached reflux. Upon reaction completion, the reaction solution was allowed to cool to room temperature at which time the product began to precipitate. The precipitate was collected by suction filtration. The cake was washed with a small amount of chilled methanol and allowed to dry on the filter overnight to give 6.25 g of a free flowing yellow powder. The compound exhibited a wavelength of maximum absorption ($\lambda_{max}$) at 375.5 nm and a molar absorptivity ($\epsilon$) of 22,300 as determined by Ultraviolet-Visible light spectroscopy (UV-Vis) in DMF solvent.

Example 128

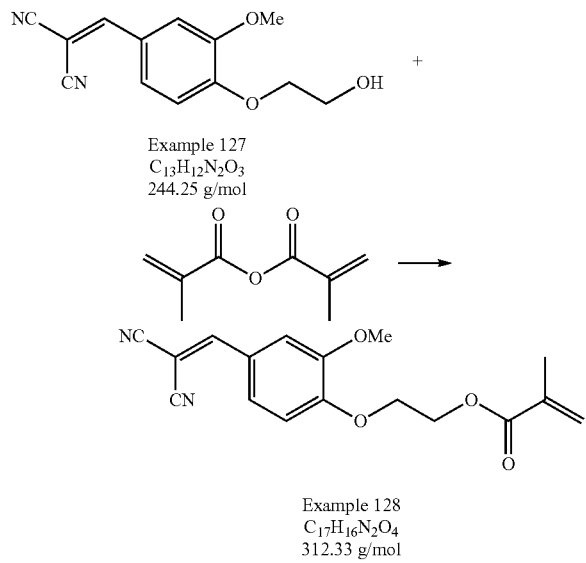

Example 127
$C_{13}H_{12}N_2O_3$
244.25 g/mol

Example 128
$C_{17}H_{16}N_2O_4$
312.33 g/mol

To a clean, dry 100 mL round bottomed flask equipped with a magnetic stirrer and reflux condenser were added 40 mL of acetone, 2.93 g of product from Example 128 (12.0 mmols), 2.5 mL of methacrylic anhydride (16.8 mmols), 2.0 mL of triethylamine (14.4 mmols), 0.07 g of 4-dimethylaminopyridine (DMAP, 0.6 mmol) and 40 mg of hydroquinone. The reaction mixture was heated to 50° C. with stirring for about 30 min at which time TLC analysis revealed that all of the starting material (Example 127) had been consumed (TLC; 1:1 tetrahydrofuran/cyclohexane). The reaction mixture was allowed to cool to room temperature then transferred to a 300 mL flask equipped with a mechanical stirrer. A 3:1 (by volume) solution of methanol and water (90 mL), respectively, was added with stirring at a dropwise rate followed by the dropwise addition of 60 mL of ice cold water. The product precipitated to give a sticky, but filterable, material. The precipitate was collected by suction filtration and washed with a small amount of cold methanol. The cake was allowed to dry on the filter overnight to give 2.56 g of a yellow solid. The compound exhibited a wavelength of maximum absorption ($\lambda_{max}$) at 372.7 nm and a molar absorptivity ($\epsilon$) of 14,400 as determined by Ultraviolet-Visible light spectroscopy (UV-Vis) in DMF solvent.

Example 129

$C_6H_7N$
93.13 g/mol $C_7H_7Cl$
126.59 g/mol

Example 129
$C_{20}H_{19}N$
273.38 g/mol

To a clean, dry 2 L flask equipped with a mechanical stirrer were added 100 g of aniline (1.07 mols), 248 mL of benzylchloride (2.16 mols), 176.2 g of sodium acetate and 1.0 g of pulverized potassium iodide. The reaction mixture was heated on a steam bath with stirring overnight. The reaction mixture was allowed to cool to room temperature then poured into a 4 L beaker containing 1 L of ice water and 200 mL of concentrated ammonium hydroxide. An oily product came out of solution that solidified upon sitting. The solid was collected by suction filtration and washed with water. The solid was crushed and slurried in methanol. A small amount of ammonium hydroxide was added then filtered. The resulting cake was washed with methanol, water and again with methanol. The cake was allowed to dry on the filter overnight to give 266.3 g of Example 129. The product was recrystallized from 800 mL of isopropyl alcohol to give 243.8 g of Example 129 as an off white solid. Field desorption mass spectrometry was used to confirm the identity of the product.

Example 130

Example 129
$C_{20}H_{19}N$
273.38 g/mol

POCl$_3$, DMF

Example 130
$C_{21}H_{19}NO$
301.39 g/mol

To a clean, dry 500 mL flask equipped with a heating mantle and addition funnel were added 150 mL of DMF and 41.0 g of the product from Example 129 (0.15 mol). The reaction vessel was purged with nitrogen and 15.4 mL of phosphorus oxychloride (0.15 mol) were added at such a rate to keep the temperature from exceeding 35° C. The reaction vessel was heated to 80-90° C. and stirring for about 2.5 h. The reaction mixture was allowed to cool to room temperature and poured into a mechanically stirred 4 L beaker containing ice water mixture (1.2 L) containing 75 mL of concentrated ammonium hydroxide. A light tan precipitate formed that was collected by suction filtration and washed with water. The cake was allowed to dry on the filter overnight to give 44.8 g of product.

Example 131

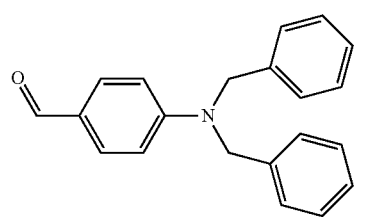

Example 130
C$_{21}$H$_{19}$NO
301.39 g/mol

+

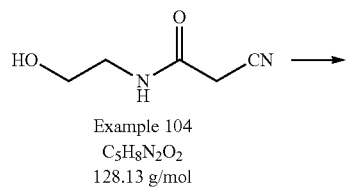

Example 104
C$_5$H$_8$N$_2$O$_2$
128.13 g/mol

→

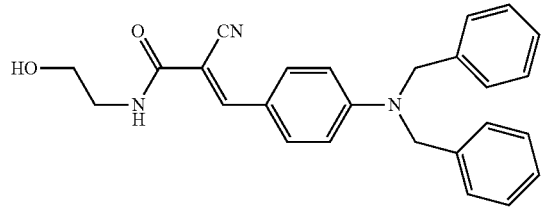

Example 131
C$_{26}$H$_{25}$N$_3$O$_2$
411.51 g/mol

To a clean, dry 500 mL round bottomed flask equipped with a magnetic stirrer and reflux condenser were added 85 mL of methanol, 4.26 g of product from Example 104 (30.0 mmols), 7.53 g of the product from Example 130 (25.0 mmols) and a few crystals of piperidine acetate. The reaction mixture was heated to reflux for 3 h and allowed to cool to room temperature. The product did not precipitate upon cooling. The reaction solution was transferred to a Coors dish and the solvent was allowed to evaporate. The remaining residue solidified upon standing to give 10.7 g of Example 131. The identity of the product was determined to be the target compound by HPLC-MS and the purity was estimated to be about 91%. The compound exhibited a wavelength of maximum absorption ($\lambda_{max}$) at 380.7 nm and a molar absorptivity ($\epsilon$) of 24,600 as determined by Ultraviolet-Visible light spectroscopy (UV-Vis) in DMF solvent.

Example 132

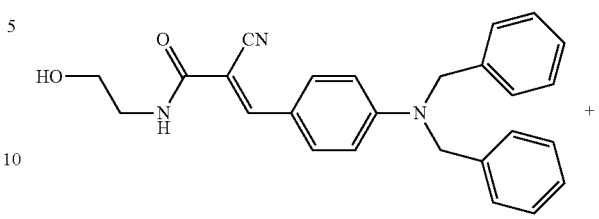

Example 131
C$_{26}$H$_{25}$N$_3$O$_2$
411.51 g/mol

+

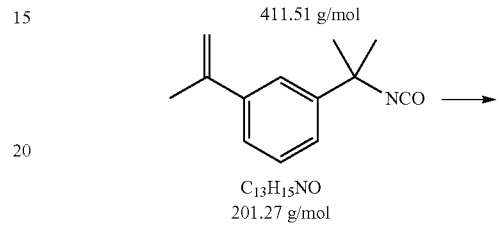

C$_{13}$H$_{15}$NO
201.27 g/mol

→

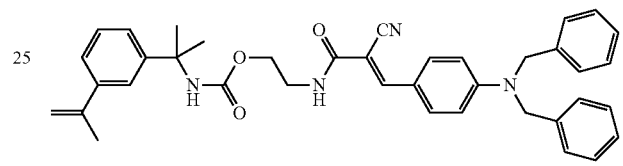

Example 132
C$_{39}$H$_{40}$N$_4$O$_3$
612.78 g/mol

To a 100 mL round bottomed flask equipped with a magnetic stirrer and heating mantle were added 30 mL of toluene, 1.2 g of 3-isopropenyl-α,α'-dimethylbenzylisocyanate (6.0 mmols), 2.06 g of the product from example 131 (5 mmols) and 3 drops of dibutyltin dilaurate. The reaction mixture was heated to 90-95° C. After about 1 h, TLC analysis revealed that some of Example 131 remained (1:1 THF/Cyclohexane) and some insoluble material remained that was believed to be starting material. Another 10 mL of toluene were added and stirring was continued at 90-95° C. for an additional 1 h. The reaction mixture was allowed to cool to room temperature and added dropwise to a 500 mL beaker containing 40 mL of heptane with stirring to precipitate the product. An oily material separated. The mother liquor was drowned into a 500 mL beaker containing 100 mL of ice cold heptane. A soft solid precipitate formed that was added to fresh, ice cold heptane, which led to the formation of a hard, filterable solid. The light yellow solid was collected by suction filtration, washed with cold heptane and allowed to dry on the filter overnight to give 0.57 g of product. The identity of the product was determined to be the target compound by HPLC-MS and the purity was estimated to be about 87%. The compound exhibited a wavelength of maximum absorption ($\lambda_{max}$) at 382.07 nm and a molar absorptivity ($\epsilon$) of 29,300 as determined by Ultraviolet-Visible light spectroscopy (UV-Vis) in DMF solvent.

Preparation of Lens Material

Example 133

Preparation of Stock Monomer Mixture

A stock mixture (50 g) of monomers suitable for preparing intraocular lens material was prepared by thoroughly mixing 2-phenylethyl acrylate (66 weight percent, PEA, CAS#3530-36-7), 2-phenylethyl methacrylate (30.5 weight percent, PEMA, CAS#3683-12-3) and 1,4-butanediol diacrylate (3.5 weight percent, BDDA, CAS#1070-70-8).

Example 134

Control

To a 20 mL vial were added 10 g of the stock mixture and 2,2'-azobisisobutyronitrile (52.3 mg, CAS#78-67-1, thermal initiator) then mixed until a solution was obtained. About 2 g of the resulting solution were added to an 18 mm×150 mm test tube using a syringe. Polymerization was initiated by heating the test tube to 65° C. in a vacuum oven under nitrogen for 17 h then heating to 100° C. for an additional 3 h. The tubes were removed from the oven and allowed to cool to room temperature. The resulting polymer was removed using a spatula. The polymer was placed in a vial containing about 25 mL of acetone and crushed into small pieces using a spatula. The polymer pieces were placed into a Soxhlet extractor and extracted with refluxing acetone for 4 to 5 h. The polymer was removed, allowed to dry on a watch glass overnight then dried at 50° C. in a vacuum over at a pressure of about 15 mm of Hg for 1 h.

Example 135

To a 20 mL vial were added 10.7 mg of the yellow polymerizable product of Example 107 and 10 g of the stock mixture to give a final concentration of about 0.1 weight percent. The mixture was stirred with gentle heating (about 50° C.) until a solution was obtain and allowed to cool to room temperature. A thermal polymerization initiator, 2,2'-azobisisobutyronitrile (52.3 mg, CAS#78-67-1), was added and mixed until a solution was obtained. About 2 g of the resulting solution was added to an 18 mm×150 mm test tube using a syringe. Polymerization was initiated by heating the test tube to 65° C. in a vacuum oven under nitrogen for 17 h then heating to 100° C. for an additional 3 h. The tubes were removed from the oven and allowed to cool to room temperature. The resulting polymer was removed using a spatula. The polymer was placed in a vial containing about 25 mL of acetone and crushed into small pieces using a spatula. The polymer pieces were placed into a Soxhlet extractor and extracted with refluxing acetone for 4 to 5 h. No color was observed in the Soxhlet vessel indicating that the yellow compound had polymerized with the monomers during polymerization. The polymer was removed, allowed to dry on a watch glass overnight then dried at 50° C. in a vacuum over at a pressure of about 15 mm of Hg for 1 h.

Example 136

To a 20 mL vial were added 10.7 mg of the UV light absorbing polymerizable product of Example 120 and 10 g of the stock mixture to give a final concentration of about 0.1 weight percent. The mixture was stirred with gentle heating (about 50° C.) until a solution was obtain and allowed to cool to room temperature. A thermal polymerization initiator, 2,2'-azobisisobutyronitrile (53.1 mg, CAS#78-67-1), was added and mixed until a solution was obtained. About 2 g of the resulting solution were added to an 18 mm×150 mm test tube using a syringe. Polymerization was initiated by heating the test tube to 65° C. in a vacuum oven under nitrogen for 17 h then heating to 100° C. for an additional 3 h. The tubes were removed from the oven and allowed to cool to room temperature. The resulting polymer was removed using a spatula. The polymer was placed in a vial containing about 25 mL of acetone and crushed into small pieces using a spatula. The polymer pieces were placed into a Soxhlet extractor and extracted with refluxing acetone for 4 to 5 h. No color was observed in the Soxhlet vessel, indicating that the compound had polymerized with the monomers during polymerization. The polymer was removed, allowed to dry on a watch glass overnight then dried at 50° C. in a vacuum over at a pressure of about 15 mm of Hg for 1 h.

All patents, publications and abstracts cited above are incorporated herein by reference in their entirety provided that to the extent any definitions in such patents, publications, and abstracts conflict with those in the present application, the definitions herein shall control with respect to the text herein and each conflicting definition in a patent, publication, or abstract shall control with respect to the content of the document containing such conflicting definitions. It should be understood that the foregoing relates only to preferred embodiments of the present invention and that numerous modifications or alterations can be made therein without departing from the spirit and the scope of the present invention as defined in the following claims.

What is claimed is:

1. A polymer comprising at least one residue of a molecule having a molecular structure depicted by Formula II:

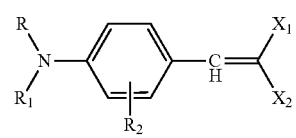

wherein:

R and $R_1$ are independently selected from $C_1$-$C_{12}$-alkyl, substituted $C_1$-$C_{12}$-alkyl, aryl, heteroaryl, $C_3$-$C_8$-cycloalkyl, $C_3$-$C_8$-alkenyl, —(CHR'CHR"O—)$_n$—$R_4$, $C_1$-$C_6$-alkylsulfonyl, arylsulfonyl, $C_1$-$C_{12}$-acyl, substituted-$C_1$-$C_{12}$-acyl, -L-Q and -Q; or R and $R_1$ are combined to make phthalimido, succinimido, morpholino, thiomorpholino, pyrrolidino, piperidino, piperazino, or thiomorpholino-S,S-dioxide;

$R_2$ is selected from hydrogen or one or two groups selected from $C_1$-$C_6$ alkyl, $C_1$-$C_6$ alkoxy and halogen;

$X_1$ and $X_2$ are independently selected from cyano, —$CO_2C_1$-$C_6$-alkylsulfonyl, arylsulfonyl, carbamoyl, $C_1$-$C_6$-alkanoyl, aroyl, aryl, heteroaryl and —COY;

R' and R" are independently selected from hydrogen and $C_1$-$C_{12}$-alkyl;

$R_4$ is selected from hydrogen, $C_1$-$C_{12}$alkyl, $C_1$-$C_6$-alkanoyl and aryl;

Y is selected from —O-L-Q, —NR'-L-Q, —N-(L-Q)$_2$, and —$R_5$;

L is a divalent organic radical selected from $C_1$-$C_6$-alkylene-O—, $C_1$-$C_6$-alkylene-NR'—; arylene-$C_1$-$C_6$-alkylene-O—, arylene-$C_1$-$C_6$-alkylene-NR'—, arylene-O(CHR'CHR"O)$_n$—, $C_1$-$C_6$-alkylene-$Y_1$—(CHR'CHR"O—)$_n$—, and —(CHR'CHR"O—)$_n$—;

$Y_1$ is selected from —O—, —S—, —$SO_2$—, —N($SO_2R_5$)—, and —N($COR_5$)—;

n is an integer between from 1 to about 1000;

$R_5$ is $C_1$-$C_{12}$-alkyl, substituted $C_1$-$C_{12}$-alkyl, $C_3$-$C_8$-cycloalkyl or aryl;

Q is a group that comprises an ethylenically unsaturated polymerizable group;

the molecule, before copolymerization, comprises at least one Q group; and the residue comprises a reaction product of saturation of the Q group.

2. A composition comprising the polymer of claim 1.

3. The polymer of claim 1, wherein:

R and $R_1$ are independently selected from the group consisting of $C_1$-$C_{12}$-alkyl, substituted $C_1$-$C_{12}$-alkyl, and aryl; or R and $R_1$ are combined to make phthalimido, succinimido, morpholino, thiomorpholino, pyrrolidino, piperidino, piperazino, or thiomorpholino-S,S-dioxide;

$R_2$ is selected from the group consisting of hydrogen, $C_1$-$C_6$ alkyl and halogen;

$X_1$ is selected from the group consisting of cyano, —$CO_2C_1$-$C_6$-alkyl, $C_1$-$C_6$-alkylsulfonyl, arylsulfonyl, carbamoyl, $C_1$-$C_6$-alkanoyl, aroyl, aryl, heteroaryl and —COY;

$X_2$ is —COY;

R' is selected from the group consisting of hydrogen and $C_1$-$C_{12}$-alkyl;

Y is selected from the group consisting of —O-L-Q, —NR'-L-Q, and —N-(L-Q)$_2$;

L is $C_1$-$C_6$-alkylene-O; and

Q is selected from the group consisting of:

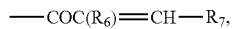
(a)

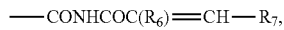
(b)

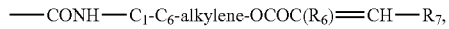
(c)

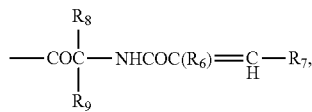
(d)

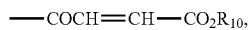
(e)

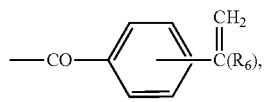
(f)

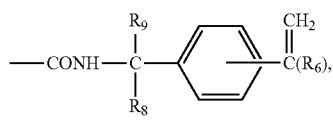
(g)

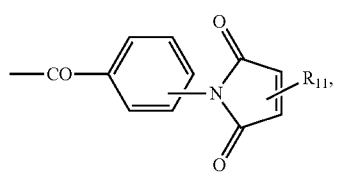
(h)

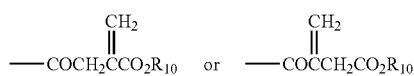
(i)

wherein:

$R_6$ is selected from the group consisting of hydrogen and $C_1$-$C_6$-alkyl;

$R_7$ is selected from the group consisting of: hydrogen; $C_1$-$C_6$ alkyl; phenyl; phenyl substituted with one or more groups selected from $C_1$-$C_6$-alkyl, $C_1$-$C_6$-alkoxy, —N($C_1$-$C_6$-alkyl)$_2$, nitro, cyano, $C_1$-$C_6$-alkoxycarbonyl, $C_1$-$C_6$-alkanoyloxy and halogen; 1- or 2-naphthyl; 1- or 2-naphthyl substituted with $C_1$-$C_6$-alkyl or $C_1$-$C_6$-alkoxy; 2- or 3-thienyl; 2- or 3-thienyl substituted with $C_1$-$C_6$-alkyl or halogen; 2- or 3-furyl; or 2- or 3-furyl substituted with $C_1$-$C_6$-alkyl;

$R_8$ and $R_9$ are independently selected from the group consisting of hydrogen, $C_1$-$C_6$-alkyl, and aryl; or $R_8$ and $R_9$ are combined to form a —(CH$_2$)$_{3-5}$ radical;

$R_{10}$ is selected from the group consisting of hydrogen, $C_1$-$C_6$-alkyl, $C_1$-$C_8$-alkenyl, $C_3$-$C_8$-cycloalkyl and aryl; and $R_{11}$ is selected from the group consisting of hydrogen, $C_1$-$C_6$-alkyl and aryl.

4. The polymer of claim 1, wherein:

R and $R_1$ are independently selected the group consisting of from methyl, ethyl, —CH$_2$CH$_2$CN, —CH$_2$CH$_2$OCOCH$_3$, and —CH$_2$CH(CH$_3$)OCOCH$_3$; or R and $R_1$ are combined to make thiomorpholino-S,S-dioxide;

$R_2$ is hydrogen;

$X_1$ is cyano;

$X_2$ is —COY;

Y is selected from the group consisting of —O-L-Q, —NR'-L-Q, and —N-(L-Q)$_2$;

R' is hydrogen;

L is selected from the group consisting of —CH$_2$CH$_2$—O—, and —CH$_2$CH(CH$_3$)—O—; and Q is —C(O)C($R_6$)=CH$R_7$, wherein $R_6$ is selected from the group consisting of hydrogen and $C_1$-$C_6$-alkyl; and $R_7$ is selected from the group consisting of: hydrogen; $C_1$-$C_6$ alkyl; phenyl; phenyl substituted with one or more groups selected from $C_1$-$C_6$-alkyl, $C_1$-$C_6$-alkoxy, —N($C_1$-$C_6$-alkyl)$_2$, nitro, cyano, $C_1$-$C_6$-alkoxycarbonyl, $C_1$-$C_6$-alkanoyloxy and halogen; 1- or 2-naphthyl; 1- or 2-naphthyl substituted with $C_1$-$C_6$-alkyl or $C_1$-$C_6$-alkoxy; 2- or 3-thienyl; 2- or 3-thienyl substituted with $C_1$-$C_6$-alkyl or halogen; 2- or 3-furyl; or 2- or 3-furyl substituted with $C_1$-$C_6$-alkyl.

5. The polymer of claim 1, wherein:

R and $R_1$ are combined to form thiomorpholino-S,S-dioxide;

$R_2$ is hydrogen;

$X_1$ is cyano;

$X_2$ is —COY;

Y is selected from the group consisting of —O-L-Q, —NR'-L-Q, and —N-(L-Q)$_2$;

R' is hydrogen;

L is selected from the group consisting of —CH$_2$CH$_2$—O—, and —CH$_2$CH(CH$_3$)—O—; and Q is —C(O)C($R_6$)=CH$R_7$, wherein $R_6$ is methyl and $R_7$ is hydrogen.

6. The polymer of claim 1, wherein:

R and $R_1$ are each —CH$_2$CH$_2$—CN;

$R_2$ is hydrogen;

$X_1$ is cyano;

$X_2$ is —COY;

R' is hydrogen;

Y is selected from the group consisting of —O-L-Q, —NR'-L-Q, and —N-(L-Q)$_2$;

L is selected from the group consisting of —CH$_2$CH$_2$—O—, and —CH$_2$CH(CH$_3$)—O—; and Q is —C(O)C($R_6$)=CH$R_7$, wherein $R_6$ is methyl and $R_7$ is hydrogen.

7. The polymer of claim 1, wherein:

R and $R_1$ are independently selected from the group consisting of —CH$_2$CH$_2$CN, —CH$_2$CH$_2$Cl, —CH$_2$CH$_2$—

OCO—C$_1$-C$_4$-alkyl, —CH$_2$CH$_2$OCO-aryl, —CH$_2$CH$_2$—OC(O)NH-aryl,

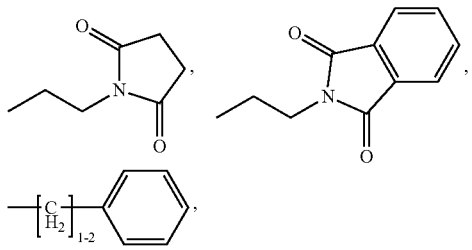

—C$_1$-C$_4$-alkyl, and —CH$_2$C$_6$H$_4$CO$_2$—C$_1$-C$_4$-alkyl; or R and R$_1$ are combined to form thiomorpholino-S,S-dioxide;

Y is —NH-L-Q;

L is selected from the group consisting of —CH$_2$CH$_2$O—, —CH$_2$CH(CH$_3$)O—, —(CH$_2$)$_3$O—, —(CH$_2$)$_4$O—, —(CH$_2$)$_6$O—, —CH$_2$C(CH$_3$)$_2$CH$_2$O—, —CH$_2$C$_6$H$_{10}$—CH$_2$O—, —C$_6$H$_4$—CH$_2$CH$_2$O—, —C$_6$H$_4$—OCH$_2$CH$_2$O—, and —CH$_2$CH$_2$(OCH$_2$CH$_2$)$_{1\text{-}3}$O—; and Q is

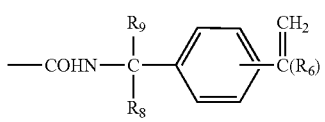

wherein R$_6$ is methyl; R$_8$ and R$_9$ are methyl.

8. The polymer of claim 1, wherein:

R and R$_1$ are independently selected from the group consisting of —CH$_2$CH$_2$CN, —CH$_2$CH$_2$Cl, —CH$_2$CH$_2$—OCO—C$_1$-C$_4$-alkyl, —CH$_2$CH$_2$OCO-aryl, —CH$_2$CH$_2$—OC(O)NH-aryl,

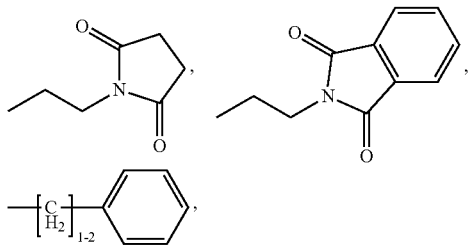

—C$_1$-C$_4$-alkyl, and —CH$_2$C$_6$H$_4$CO$_2$—C$_1$-C$_4$-alkyl; or R and R$_1$ are combined to form thiomorpholino-S,S-dioxide;

Y is —NH-L-Q;

L is selected from the group consisting of —CH$_2$CH$_2$O—, —CH$_2$CH(CH$_3$)O, —(CH$_2$)$_3$O—, —(CH$_2$)$_4$O—, —(CH$_2$)$_6$O—, —CH$_2$C(CH$_3$)$_2$CH$_2$O—, —CH$_2$C$_6$H$_{10}$CH$_2$O—, —C$_6$H$_4$CH$_2$CH$_2$O—, —C$_6$H$_4$—OCH$_2$CH$_2$O—, or —CH$_2$CH$_2$(OCH$_2$CH$_2$)$_{1\text{-}3}$O—; and Q is —C(O)C(R$_6$)=CHR$_7$, wherein R$_6$ is methyl and R$_7$ is hydrogen.

9. The polymer of claim 1, wherein:

R is —CH$_2$CH$_2$CN;

R$_1$ is selected from the group consisting of —CH$_2$CH$_2$CN, —CH$_2$CH$_2$Cl, —CH$_2$CH$_2$OCO—C$_1$-C$_4$-alkyl,

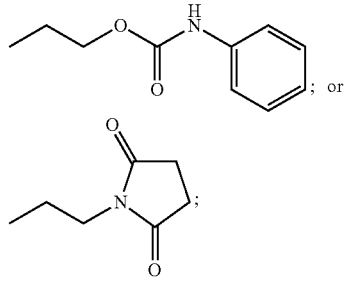

Y is —NH-L-Q;

L is selected from the group consisting of —CH$_2$CH$_2$O— and —CH$_2$CH(CH$_3$)O—; and Q is

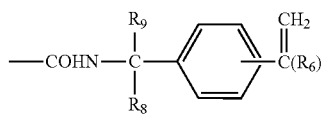

wherein R$_6$, R$_8$ and R$_9$ are methyl.

10. The polymer of claim 1, wherein:

R is —CH$_2$CH$_2$CN;

R$_1$ is selected from the group consisting of —CH$_2$CH$_2$CN, —CH$_2$CH$_2$Cl, —CH$_2$CH$_2$OCO—C$_1$-C$_4$-alkyl,

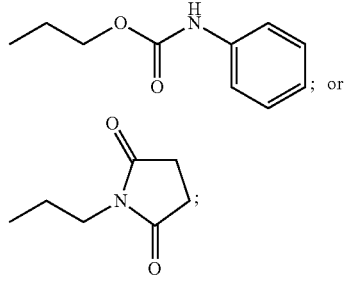

Y is —NH-L-Q;

L is selected from the group consisting of —CH$_2$CH$_2$O— and —CH$_2$CH(CH$_3$)O—; and Q is —C(O)C(R$_6$)=CHR$_7$, wherein R$_6$ is methyl and R$_7$ is hydrogen.

11. The polymer of claim 1, wherein the molecule having the molecular structure depicted by Formula II has a following formula VII:

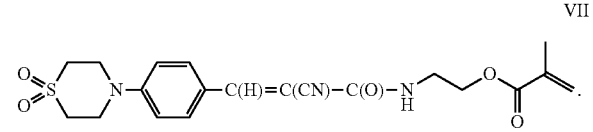

VII

* * * * *